(12) United States Patent
Rakuma et al.

(10) Patent No.: US 8,397,523 B2
(45) Date of Patent: Mar. 19, 2013

(54) ELECTROLYTIC WATER GENERATING DEVICE, AIR FILTERING SYSTEM, AIR CONDITIONING AND FILTERING APPARATUS, AND AIR CONDITIONING AND FILTERING SYSTEM

(75) Inventors: Tsuyoshi Rakuma, Ora-gun (JP); Junichi Saito, Ashikaga (JP); Takuro Nishihara, Ota (JP); Toru Arakawa, Tatebayashi (JP); Hiroyuki Kobayashi, Ora-gun (JP)

(73) Assignee: SANYO Electric Co., Ltd., Moriguchi-shi (JP)

( * ) Notice: Subject to any disclaimer, the term of this patent is extended or adjusted under 35 U.S.C. 154(b) by 965 days.

(21) Appl. No.: 12/473,565

(22) Filed: May 28, 2009

(65) Prior Publication Data

US 2009/0293527 A1    Dec. 3, 2009

(30) Foreign Application Priority Data

May 30, 2008 (JP) ................. 2008-142641
Sep. 19, 2008 (JP) ................. 2008-241179

(51) Int. Cl.
*F28C 1/00* (2006.01)
*F28D 3/00* (2006.01)

(52) U.S. Cl. .......................... 62/121; 62/171
(58) Field of Classification Search ............ 62/171, 62/121, 259.4; 261/127, 146
See application file for complete search history.

(56) References Cited

U.S. PATENT DOCUMENTS

| | | | | |
|---|---|---|---|---|
| 1,583,060 A | * | 5/1926 | Lewis | 454/231 |
| 2,075,862 A | * | 4/1937 | Myers | 261/142 |
| 2,359,051 A | * | 9/1944 | Roper | 62/280 |
| 4,107,940 A | * | 8/1978 | Schlom et al. | 62/121 |

(Continued)

FOREIGN PATENT DOCUMENTS

| | | |
|---|---|---|
| JP | 06-000214 A | 1/1994 |
| JP | 10-128029 A | 5/1998 |

(Continued)

OTHER PUBLICATIONS

Japanese Office Action dated Dec. 27, 2011, issued in corresponding Japanese Patent Application No. 2008-142641.

(Continued)

*Primary Examiner* — Ljiljana Ciric
*Assistant Examiner* — Alexis Cox
(74) *Attorney, Agent, or Firm* — Westerman, Hattori, Daniels & Adrian, LLP

(57) ABSTRACT

An air filtering apparatus for filtering air includes a chamber having an air flow passage through which air flows, the chamber being connected through an air supply duct to a plurality of air blow-out ports opened to a large space, an air filtering portion that is disposed in the chamber and has a plurality of gas-liquid contact members for bringing air into contact with electrolytic water to filter the air, a water tank that is connected through a water feeding pump to a supply pipe for supplying the electrolytic water to each of the gas-liquid contact members of the air filtering portion, an electrolytic unit for generating the electrolytic water, and a mechanism for leading to the electrolytic unit a part of electrolytic water in the water tank which is sucked by the water feeding pump and supplied to the plurality of gas-liquid contact members through the supply pipe, electrolyzing the part of the electrolytic water in the electrolytic unit to further generate electrolytic water and returning the generated electrolytic water into the water tank.

10 Claims, 9 Drawing Sheets

U.S. PATENT DOCUMENTS

| | | | |
|---|---|---|---|
| 5,182,921 A * | 2/1993 | Yan | 62/235.1 |
| 5,775,114 A * | 7/1998 | Ji | 62/121 |
| 7,896,947 B2 * | 3/2011 | Takahashi et al. | 95/26 |
| 2002/0073718 A1 * | 6/2002 | Maisotsenko et al. | 62/121 |
| 2003/0150234 A1 * | 8/2003 | Ohmi et al. | 62/309 |
| 2006/0117764 A1 * | 6/2006 | Patel et al. | 62/121 |
| 2006/0273470 A1 * | 12/2006 | Takahashi et al. | 261/4 |
| 2008/0017039 A1 * | 1/2008 | Takahashi et al. | 96/240 |
| 2010/0108497 A1 * | 5/2010 | Ogawa et al. | 204/276 |

FOREIGN PATENT DOCUMENTS

| | | |
|---|---|---|
| JP | 11-179359 A | 7/1999 |
| JP | 2000-074414 A | 3/2000 |
| JP | 2000-257914 A | 9/2000 |
| JP | 2002-181358 A | 6/2002 |
| JP | 2005-270927 A | 10/2005 |
| JP | 2008-109984 A | 5/2008 |
| JP | 2008109984 A * | 5/2008 |

OTHER PUBLICATIONS

Japanese Office Action dated Jul. 24, 2012, issued in corresponding Japanese Patent Application No. 2008-241179 with English translation (31 pages).

Japanese Office Action dated Mar. 27, 2012, issued in corresponding Japanese Patent Application No. 2008-142641, (w/English translation) 8 pages.

* cited by examiner

ELECTROLYTIC WATER GENERATING DEVICE, AIR FILTERING SYSTEM, AIR CONDITIONING AND FILTERING APPARATUS, AND AIR CONDITIONING AND FILTERING SYSTEM

INCORPORATION BY REFERENCE

The present application claims priority under 35 U.S.C. §119 to Japanese Patent Application Nos. 2008-142641 filed on May 30, 2008 and 2008-241179 filed on Sep. 19, 2008. The contents of the applications are incorporated herein by reference in its entirety.

BACKGROUND OF THE INVENTION

1. Field of the Invention

The present invention relates to an air filtering system and an air conditioning and filtering system for performing sterile filtration, sterilizing, inactivating, deodorizing, etc. (hereinafter collectively referred to as "filter") on air to be supplied into a large space such as a stage theater, a movie theater, etc., and an electrolytic water generating device for these systems.

2. Description of the Related Art

There is known a rooftop type air conditioner which is disposed on the rooftop of a building and connected through an air supply duct to plural air blow-out ports opened to a large space in the building (for example, JP-A-2000-74414). This type of air conditioner includes a heat-source side unit having a compressor and a hat-source side heat exchanger, and a use-side unit having an air blower and a use-side heat exchanger which are provided integrally with each other, and air-conditioned air heat-exchanged in the use-side unit is supplied to each air blow-out port through the air supply duct.

The rooftop type air conditioner is provided to large-space facilities in which an unspecified number of people stay for a long time, such as a stage theater, a movie theater, a hospital, a shopping center, etc., and thus it has been desired to supply cleaned (filtered) air into such a large space. However, a large amount of air must be supplied through the air supply duct into the respective air blow-out ports, and thus it has been difficult to filter a large amount of air to be supplied into the large space through the air blow-out ports.

Furthermore, there has been also proposed an air filtering apparatus in which tap water is electrolyzed to generate electrolytic water containing hypochlorous acid, and microorganisms such as virus, bacteria, fungus, etc. (hereinafter referred to as "virus, etc.") floating in the air are removed by using the electrolytic water concerned (for example, JP-A-2002-181358). According to this air filtering apparatus, electrolytic water is supplied to a humidifying element formed of non-woven cloth or the like to bring virus, etc. in the air into contact with the electrolytic water on the humidifying element and inactivate the virus, etc., thereby filtering air.

A device for generating electrolytic water by electrolyzing water as in the case of the air filtering apparatus as described above requires an electrical circuit unit for supplying power to an electrolytic unit. This electrical circuit unit is required to be disposed so that neither water nor electrolytic water invades into the electrical circuit unit. In order to satisfy this requirement, it may be considered that the electrical circuit unit is disposed separately from a case in which the electrolytic unit is accommodated. However, if the electrical circuit unit is far away from the electrolytic unit, etc., an efficiency of a wiring work (a layout of wires) is deteriorated, and thus the maintenance performance may be degraded.

SUMMARY OF THE INVENTION

Therefore, the present invention has been implemented in view of the foregoing situation, and has an object to provide an air filtering system and an air conditioning and filtering system that can perform sterile filtration, sterilize, inactivate, deodorize or the like (i.e., filter) air to be supplied into a large space with a simple construction.

Furthermore, another object of the present invention is to provide an electrolytic water generating device for electrolyzing water to generate electrolytic water that has excellent maintenance performance and can prevent water and/or electrolytic water from invading into an electrical circuit unit for supplying power for electrolysis and facilitate a wiring work.

In order to solve the above problem, according to a first aspect of the present invention, there is provided an air filtering apparatus for filtering air that comprises: a chamber having an air flow passage through which air flows, the chamber being connected through an air supply duct to a plurality of air blow-out ports opened to a large space; an air filtering portion that is disposed in the chamber and has a plurality of gas-liquid contact members for bringing air into contact with electrolytic water to filter the air; a water tank that is connected through a water feeding pump to a supply pipe for supplying the electrolytic water to each of the gas-liquid contact members of the air filtering portion; an electrolytic unit for generating the electrolytic water; and a mechanism for leading to the electrolytic unit a part of electrolytic water in the water tank which is sucked by the water feeding pump and supplied to the plurality of gas-liquid contact members through the supply pipe, electrolyzing the part of the electrolytic water in the electrolytic unit to further generate electrolytic water and returning the generated electrolytic water into the water tank.

According to the above air filtering apparatus, the chamber connected through the air supply duct to the plural air blow-out ports opened to the large space is provided, and the air filtering portion having the plural gas-liquid contact members for bringing air into contact with electrolytic water to filter the air is provide din the chamber. Therefore, the air filtered in the respective gas-liquid contact members of the air filtering portion is supplied to the air blow-out ports through the air supply duct, and the filtered air is broadly spread in the large space through the air blow-out ports. Accordingly, the air supplied to the large space can be filtered with a simple construction. Furthermore, the air filtering portion is concentraively provided in the chamber, and thus the maintenance of the gas-liquid contact members of the air filtering portion can be easily performed.

Furthermore, the water tank connected through the water feeding pump to the supply pipe for supplying the electrolytic water to the respective gas-liquid contact members of the air filtering portion is provided, and the electrolytic unit for generating electrolytic water is provided. Furthermore, there is also provided the mechanism for leading to the electrolytic unit a part of electrolytic water in the water tank which is sucked by the water feeding pump and supplied to the plural gas-liquid contact members through the supply pipe is provided, generating electrolytic water in the electrolytic unit, and then returning the electrolytic water into the water tank. Accordingly, the variation width of the electrolytic water concentration in the water tank can be suppressed to a small level, and a stable concentration of electrolytic water can be supplied to the respective gas-liquid contact members of the air filtering portion. Therefore, the air filtering operation at the respective gas-liquid contact members can be stably performed. Therefore, a large amount of air supplied through the air blow-out port into the large space can be uniformly filtered.

In the above air filtering apparatus, the plural gas-liquid contact members may be arranged so as to cover substantially the whole cross-sectional area of the air flow passage in the chamber.

According to this construction, the air passing in the chamber is uniformly filtered by the plural gas-liquid contact members which are arranged so as to cover substantially the whole cross-sectional area of the air flow passage, and thus a large amount of air-conditioned air supplied into the large space through the air blow-out ports can be uniformly filtered.

In the above air filtering apparatus, the gas-liquid contact members may be arranged in a vertical direction, and gas-liquid contact members covering a lower area of the air flow passage may be arranged to be displaced to the upstream side of the air flow passage with respect to gas-liquid contact members covering an upper area of the air flow passage. Furthermore, in the above air filtering apparatus, the gas-liquid contact members may be arranged in a vertical direction, and gas-liquid contact members covering a lower area of the air flow passage may be arranged to be displaced to the downstream side of the air flow passage with respect to gas-liquid contact members covering an upper area of the air flow passage.

According to this construction, the plural gas-liquid contact members whose total area is larger than the area of the opening (the cross-sectional area) of the air flow passage can be arranged coherently in the air flow passage, and thus the air filtering performance of the gas-liquid contact members arranged in the air flow passage can be enhanced.

According to a second aspect of the present invention, there is provided an air conditioning and filtering apparatus for air-conditioning and filtering air, comprising: an air conditioner that is connected through an air supply duct to a plurality of air blow-out ports opened to a large space and supplies air-conditioned air through the air supply duct to each of the air blow-out ports; an air flow passage through which the air conditioner and each of the plural air blow-out ports are connected to each other and the air-conditioned air flows; a chamber provided in the air flow passage; an air filtering portion that is provided in the chamber and has a plurality of gas-liquid contact members for bringing the air-conditioned air into contact with electrolytic water to filter the air-conditioned air; a water tank that is connected through a water feeding pump to a supply pipe for supplying the electrolytic water to each of the gas-liquid contact members of the air filtering portion; an electrolytic unit for generating the electrolytic water; and a mechanism for leading to the electrolytic unit a part of electrolytic water in the water tank which is sucked by the water feeding pump and supplied to the plurality of gas-liquid contact members through the supply pipe, electrolyzing the part of the electrolytic water in the electrolytic unit to further generate electrolytic water and returning the generated electrolytic water into the water tank.

In the above construction, the electrolytic unit for generating the electrolytic water may be directly secured to the water tank so that scale type materials generated in the electrolytic unit are returned into the water tank together with the electrolytic water.

According to this construction, scale type materials generated in the electrolytic unit in the electrolysis process are returned into the water tank together with the electrolytic water, and deposited in the water tank. Therefore, these scale type materials can be prevented from flowing through the supply pipe into the gas-liquid contact members of the air filtering portion. Therefore, blockage of the supply pipe due to flow-in of the scale type materials or clogging of the respective gas-liquid contact members can be prevented. Therefore, the maintenance frequency of the supply pipe and the gas-liquid contact members can be reduced, and the maintenance work can be lightened.

In the above air conditioning and filtering apparatus, the air conditioner may have a housing, and the housing may be compartmented into an heat exchanger chamber in which a heat exchanger and an air blower are mounted, a machine chamber in which a compressor is mounted and an air filtering chamber containing the chamber, the air conditioned air being circulated through the chamber.

According to this construction, the air filtering portion can be easily installed in the chamber which is formed in the housing of the air conditioner in advance, and thus a large amount of air supplied to the large space can be filtered without increasing the size of the apparatus and with a simple construction.

In the above air-conditioning and filtering apparatus, the air supply duct may be connected to the chamber, and the plural gas-liquid contact members may be arranged so as to cover substantially the whole cross-sectional area of the air flow passage in the chamber.

In the above air-conditioning and filtering apparatus, the gas-liquid contact members may be arranged in a vertical direction, and gas-liquid contact members covering a lower area of the air flow passage may be arranged to be displaced to the upstream side of the air flow passage with respect to gas-liquid contact members covering an upper area of the air flow passage.

In the above air conditioning and filtering apparatus, the lower end of each gas-liquid contact member may be connected through an air leading plate to the upper end of the gas-liquid contact member which is adjacent to the former gas-liquid contact member at the upstream side of the air flow passage so that the gap between both the gas-liquid contact members is closed.

In the above air conditioning and filtering apparatus, the gas-liquid contact members and the air leading plates may be arranged so as to form a corrugated arrangement in side view.

In the above conditioning and filtering apparatus, the gas-liquid contact members may be arranged in a vertical direction, and gas-liquid contact members covering a lower area of the air flow passage may be arranged to be displaced to the downstream side of the air flow passage with respect to gas-liquid contact members covering an upper area of the air flow passage.

In the above air conditioning and filtering apparatus, the lower end of each gas-liquid contact member may be connected through an air leading plate to the upper end of the gas-liquid contact member which is adjacent to the former gas-liquid contact member at the upstream side of the air flow passage so that the gap between both the gas-liquid contact members is closed.

In the above air conditioning and filtering apparatus, the gas-liquid contact members and the air leading plates may be arranged so as to form a corrugated arrangement in side view.

According to a third aspect of the present invention, there is provided an electrolytic water generating device comprising: a water tank for stocking water; an electrolytic unit that is secured to the water tank and electrolyzes water in the water tank to generate electrolytic water; an electrolytic water supply pump for supplying the electrolytic water generated by the electrolytic unit to the outside; an electrical component box containing a electrical circuit portion for supplying power to the electrolytic unit and the electrolytic water supply pump; and a case in which the water tank, the electrolytic unit, the electrolytic water supply pump and the electrical component box are accommodated, wherein the electrical component box is fixed to the case so as to be floated from the bottom surface of the case, and the electrolytic water supply pump is disposed below the electrical component box.

The above electrolytic water generating device may further comprise: a water solution tank for stocking electrolyte water solution; and a water solution supply pump for supplying the electrolyte water solution from the water solution tank to the water tank, wherein the water solution tank and the water tank are arranged in juxtaposition with each other at one side of the case, the electrolytic water supply pump and the water solution supply pump are arranged in juxtaposition with each other below the electrical component box, and the electrolytic water supply pump is located at the water tank side.

In this case, in the construction that the water solution tank for stocking electrolyte water solution and the water solution supply pump are provided in the electrolytic water generating device, the invasion of water, electrolytic waster or electrolyte water solution into the electrical (power supply) circuit portion can be prevented while the water solution tank and the water solution supply pump are disposed in the same case as the electrical component box, and thus the excellent maintenance performance can be secured. Furthermore, the water solution tank and the water tank are juxtaposed with each other at one side of the case, the electrolytic water pump is located at the water tank side below the electrical component box. Therefore, the pipes between the electrolytic water supply pump and the water tank can be shortened, the layout of pipes can be efficiently performed, and the power loss of the pump can be suppressed.

In the above electrolytic water generating device, the case may be provided with an openable service panel at one surface thereof which is far away from the water tank and the water solution tank, and under an open state of the service panel, a cover of the electrical component box may be exposed and the inside of the electrical component box can be accessed by opening the cover.

In this case, the service panel is provided at the side surface which is far away from the water tank and the water solution tank, the cover of the electrical component box is exposed by opening the service panel, and the electrical (power supply) circuit portion in the electrical component box can be accessed by opening the cover. Therefore, the access to the electrical circuit portion can be easily performed, and the excellent maintenance performance can be secured. Furthermore, the service panel is located at a position far away from the water tank and the water solution tank. Therefore, invasion of water, electrolytic water or the electrolyte water solution into the electrical circuit portion can be prevented at the access time to the electrical circuit portion, and the electrical circuit portion can be surely protected.

In the above electrolytic water generating device, the case may have a lid covering the upper ends of the upper surface of the respective side surfaces thereof, and the service panel may be allowed to be opened when the lid is opened.

In this case, the upper ends of the upper surface and the side surfaces of the case are covered by the lid. Therefore, even when the electrolytic water generating device is set outdoors or the like, the invasion of water or the like into the electrical circuit portion can be prevented. Furthermore, when the lid of the case is opened, the access to the electrical circuit portion in the electrical component box is enabled by opening the service panel. Therefore, even when the electrolytic water generating device is set outdoors or the like, the excellent maintenance performance can be secured with surely protecting the electrical circuit portion.

According to a fourth aspect of the present invention, there is provided an air filtering system including an electrolytic water generating device for generating electrolytic water and an air filtering device for bringing air into contact with the electrolytic water generated in the electrolytic water generating device to filter the air, wherein the electrolytic water generating device comprises: a water tank for stocking water; an electrolytic unit that is secured to the water tank and electrolyzes water in the water tank to generate electrolytic water; an electrolytic water supply pump for supplying the electrolytic water generated by the electrolytic unit to the outside; an electrical component box containing a electrical circuit portion for supplying power to the electrolytic unit and the electrolytic water supply pump; and a case in which the water tank, the electrolytic unit, the electrolytic water supply pump and the electrical component box are accommodated, wherein the electrical component box is fixed to the case so as to be floated from the bottom surface of the case, and the electrolytic water supply pump is disposed below the electrical component box.

According to this construction, in the electrolytic water generating device provided to the air filtering system for filtering air with electrolytic water, the electrical component box in which the electrolytic unit and the electrical circuit portion for supplying power to the electrolytic water supply pump is accommodated in the same case as the water tank, the electrolytic unit and the electrolytic water supply pump, and the electrical component box is fixed so as to be floated from the bottom surface of the case. Therefore, invasion of water or electrolytic water into the electrical circuit portion can be prevented, and the electrical circuit portion can be surely protected. Accordingly, the respective elements constituting the electrolytic water generating device can be accommodated in one case, and the excellent maintenance performance can be secured. Furthermore, the wire length between the electrical circuit portion and each of the electrolytic unit and the electrolytic water supply pump may be short, so that the layout of wires can be efficiently performed.

The above air filtering system may further comprise a chamber connected through an air supply duct to plural air blow-out ports opened to a large space is provided on the rooftop of a building having the large space, the air filtering unit is disposed in the chamber, and the electrolytic water generating device for supplying electrolytic water to the air filtering unit in the chamber is installed on the rooftop together with the chamber.

According to the above construction, the air filtering portion is provided in the chamber provide on the rooftop of the building having the large space, and the filtered air is supplied through the air supply duct into the large space, whereby the air in the large space can be cleaned. In this construction, the electrolytic water generating device installed on the rooftop is designed so that the electrical component box containing the electrical circuit portion is accommodated in the same case as the water tank, the electrolytic unit, and the electrolytic water supply pump, whereby the excellent maintenance performance can be secured and also the excellent layout of wires can be implemented. Furthermore, invasion of water or electrolytic water into the electrical circuit portion can be prevented, and the electrical circuit portion can be surely protected, so that the air filtering system for cleaning air in a large space can be easily implemented at low cost.

According to a fifth aspect of the present invention, there is provided an air conditioning and filtering system for supplying and circulating air-conditioned and filtered air in a large space, comprising: an air conditioner for air-conditioning air; an air filtering unit that is connected to the air conditioner and filters the air-conditioned air from the air conditioner by bringing the air-conditioned air from the air conditioner into contact with electrolytic water, the air conditioner and the air filtering unit being assembled in a single case; an electrolytic water supplying unit for generating electrolytic water and supplying the electrolytic water to the air filtering unit; an air supply passage through which the air-conditioned and filtered air from the air filtering unit is passed and dispersively blown into the large space; and an air return passage through which the air-conditioned and filtered air in the large space is sucked and returned to the air conditioner again.

According to the present invention, a large amount of air-conditioned air to be supplied into a large space through air blow-out ports can be filtered with a simple construction.

Furthermore, according to this invention, the respective elements constituting the electrolytic water generating device can be accommodated in one case with preventing invasion of water or electrolytic water into the electrical circuit portion. Therefore, the excellent maintenance performance can be secured, and the wire length between the electrical circuit portion and each of the electrolytic unit and the electrolytic water supply pump can be shortened, so that the layout of wires can be efficiently implemented.

DETAILED DESCRIPTION OF THE PREFERRED EMBODIMENTS

Preferred embodiments according to the present invention will be described hereunder with reference to the accompanying drawings.

Figure 1:
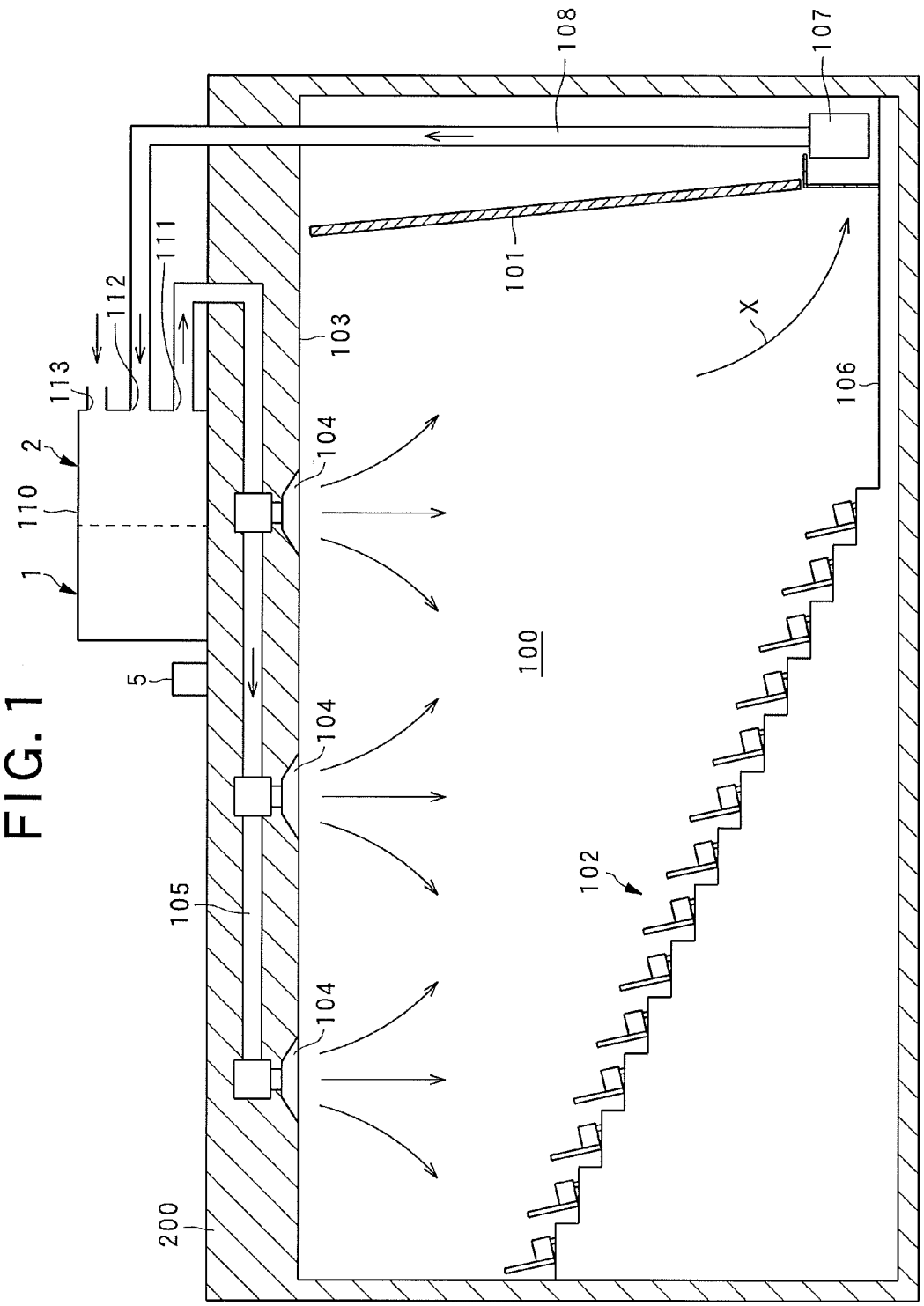
FIG. 1 is a cross-sectional view showing a state that a rooftop type air conditioner according to a first embodiment is disposed in a building.

FIG. 1 is a diagram showing a movie theater 100 (hereinafter referred to as "theater") as large-space facilities in which a rooftop type air conditioner (hereinafter referred to as air conditioner) 100 according to an embodiment of the present invention is disposed.

In the first embodiment, such a situation that an air conditioner 110 is disposed in the theater 100 as one example of the large-space facilities will be described.

As shown in FIG. 1, a screen 101 is disposed at the front side of the theater 100, and audience seat portions 102 are provided in a staircase pattern at the middle and rear side of the theater 100 so as to face the screen 101. Furthermore, plural air blow-out ports 104 for blowing air-conditioned air supplied from the air conditioner 110 into the inside of the theater 100 are provided to the ceiling portion 103 of the theater 100. These air blow-out ports 104 are connected to the air supply port 111 of the air conditioner 110 through an air supply duct 105. The air blow-out ports 104 may be provided to the ceiling portion in any arrangement style, for example, they may be disposed dispersively, uniformly or locally.

Furthermore, a floor portion 106 of the theater 100 is provided with an air suction port 107 for sucking air inside the theater (indoor air) in the neighborhood of the floor portion 106. The air suction port 107 is provided behind the screen 101 when viewed from the locating side of the audience seat portions 102, and connected to an indoor air introducing port 112 of the air conditioner 110 through an air suction duct 108 extending upwardly in the back space of the screen 101. The air conditioner 110 is further provided with an outdoor introducing port 113 for introducing air in the open air (outdoor air) into the air conditioner 110.

As indicated by an arrow X, air in the theater 100 (indoor air) is sucked from the air suction port 107, passed through the air suction duct 108 and the indoor air introducing port 112 and introduced into the air conditioner 110. Here, outdoor air is also introduced through the outdoor air introducing port 113 into the air conditioner 110, and thus the outdoor air and the indoor air are mixed in the air conditioner 110. The mixed air is heat-exchanged in a use-side heat exchanger (described later) provided to the air conditioner 110, passed through the air supply port 111 and the air supply duct 105 and then supplied as air-conditioned air from the air blow-out ports 104 into the theater 100.

The air conditioner 110 is disposed on the rooftop of a structure (building) 200 having large-space facilities in which an unspecified number of people stay for a long time, such as a movie theater, a stage theater, a hospital, a shopping center or the like, for example, and air-conditions the large space (large-space room) beneath or in the neighborhood of the setup place of the air conditioner 110.

Figure 2:
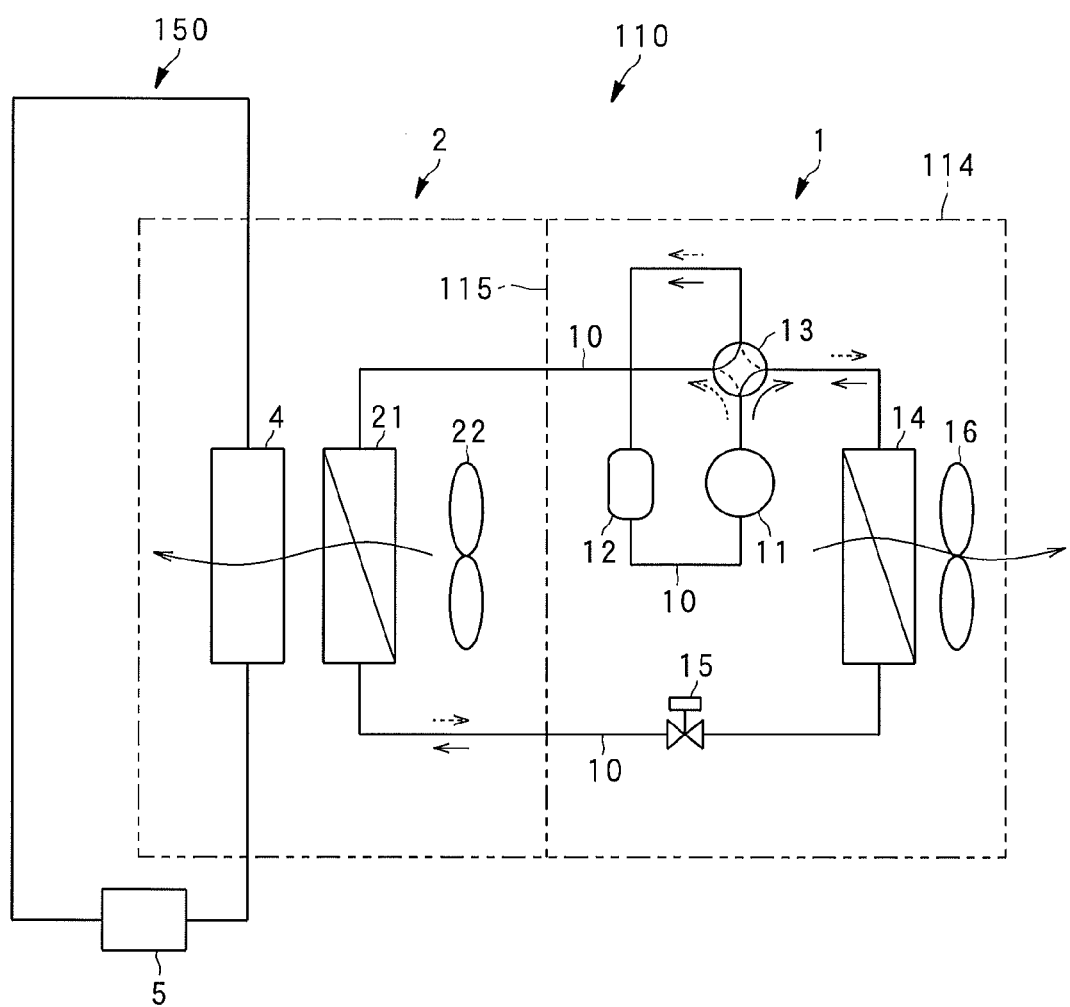
FIG. 2 is a schematic diagram showing the construction of the air conditioner shown in FIG. 1.
Figure 3:
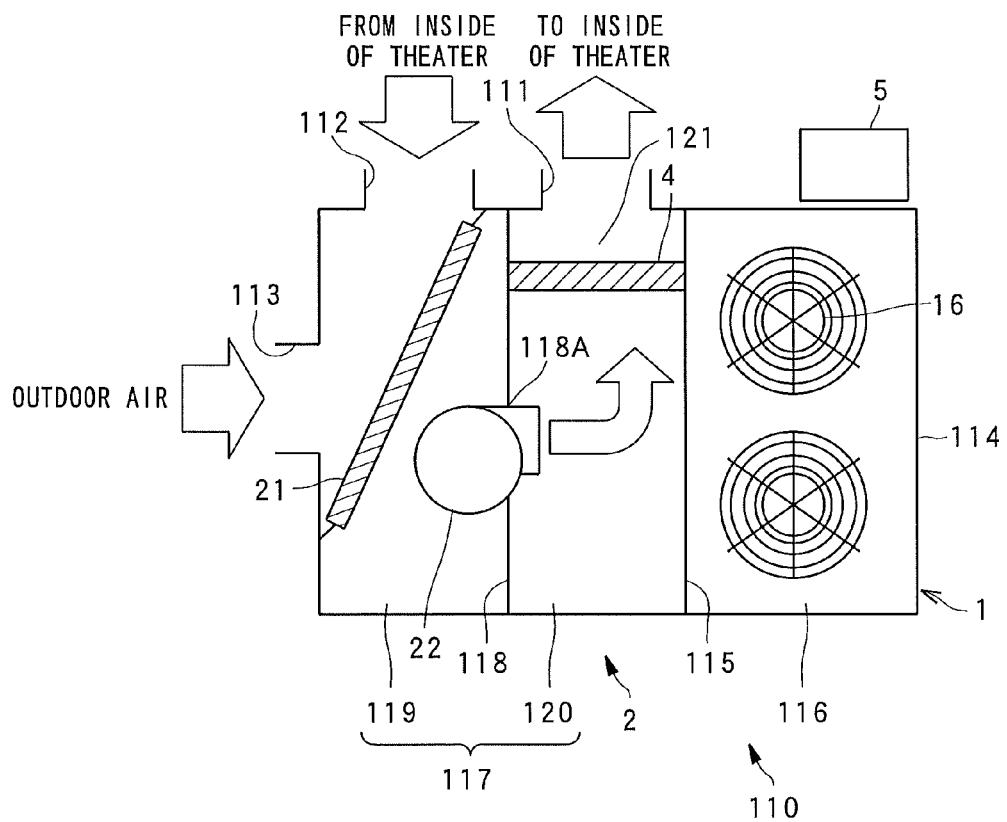
FIG. 3 is a top view showing the internal construction of the air conditioner.

FIGS. 2 and 3 are diagrams showing the construction of the air conditioner 110. FIG. 2 is a diagram showing the construction of the air conditioner 110, and FIG. 3 is a schematic diagram showing air flow into/from the air conditioner 110.

As shown in FIGS. 2 and 3, the air conditioner 110 includes a heat-source side unit 1 and a use-side unit 2 which are disposed integrally with each other in one housing 114.

Specifically, the inside of the housing 114 is compartmented into two chambers by a partition plate 115, and the heat-source side unit 1 is disposed in one chamber (machine chamber) while the use-side unit 2 is disposed in the other chamber 117. The heat-source side unit 1 and the use-side unit 2 are connected to each other through a refrigerant pipe 10 to form a refrigerant circuit.

As shown in FIG. 2, the heat-source side unit 1 has a compressor 111 provided to the refrigerant pipe 10. An accumulator 12 is connected to the suction side of the compressor 11, and a four-way valve 13, a thermal-source side heat exchanger 14 and an electric expansion valve 15 are successively connected to the discharge side of the compressor 11 in this order. Furthermore, a heat-source side air blower 16 for blowing air to the heat-source side heat exchanger 14 is disposed in the heat-source side unit 1.

Furthermore, the use-side unit 2 is provided with a use-side heat exchanger 21 connected to the electric expansion valve 15 through the refrigerant pipe 10, and a use-side air blower 22 for blowing air to the use-side heat exchanger 21. The use-side heat exchanger 21 is connected to the four-way valve 13 through the refrigerant pipe 10.

Under cooling operation, the four-way valve 13 is switched so that refrigerant flows in a direction indicated by a solid-line arrow of FIG. 2. High-pressure refrigerant discharged from the compressor 11 passes through the accumulator 12 and reaches the heat-side heat exchanger 14, and then it is condensed in the heat-source side heat exchanger 14 and fed to the electric expansion valve 15. The high-pressure refrigerant expands in the electrical expansion valve 15 and flows into the use-side heat exchanger 21, and then evaporates in the use-side heat exchanger 21 to cool air introduced into the use-side unit 2. The refrigerant evaporating in the use-side heat exchanger 21 is returned into the suction side of the compressor 11.

Under heating operation, the four-way valve 13 is switched so that refrigerant flows in a direction indicated by a broken-line arrow shown in FIG. 2. The high-pressure refrigerant discharged from the compressor 11 is fed to the use-side heat exchanger 21, and condensed in the use-side heat exchanger 21, whereby air introduced into the use-side unit 2 is humidified. The refrigerant condensed in the use-side heat exchanger 21 expands in the electrical expansion valve 15, flows into the heat-source side heat exchanger 14 and then evaporates in the heat-source side heat exchanger 14. Thereafter, it is fed through the four-way valve 13 into the accumulator 12, and then returned to the suction side of the compressor 11.

The air conditioner 110 is provided with an air filtering unit 150 for filtering air-conditioned air which is heated or heated in the use-side heat exchanger 21 under operation of the use-side air blower 22. An air conditioning and filtering system according to this embodiment is constructed by the air conditioner 110 and the air filtering unit 150 equipped in the air conditioner 110. More specifically, in addition to the air conditioner 110 and the air filtering unit 150, the air conditioning and filtering system is further constructed by an air-conditioned and filtered air circulating passage for supplying the air-conditioned and filtered air from the air conditioner 110 and the air filtering unit 150 through the plural air blow-out ports 104 on the ceiling portion of large-space facilities (a theater, a hospital or the like) into the large space, sucking air in the large space and then returned the air into the air conditioner 110 and the air filtering unit 150. The air filtering unit 150 corresponds to an air filtering system.

As shown in FIG. 2, the air filtering unit 150 has an air filtering portion 4 for bringing air introduced to the use-side unit 2 into contact with electrolytic water containing active oxygen species to filter (sterilize, inactivate, deodorize or the like) the air, and an electrolytic water circulating and supplying portion 5 for electrolyzing water containing predetermined ion species to generate the electrolytic water containing the active oxygen species, and circulating and supplying the electrolytic water to the air filtering portion 4.

As shown in FIG. 3, the other chamber 117 in which the use-side unit 2 is provided is further compartmented into a heat exchange chamber 119 and an air filtering chamber 120.

An indoor air introducing port 112 and an outdoor air introducing port 113 are formed in the heat exchange chamber 119, and the use-side heat exchanger 21 is disposed at the downstream side of the indoor introducing port 112 and the outdoor introducing port 113 in a bracing-shaped manner (so as to be oblique to the air flow from the indoor air introducing port 112 and the air flow from the outdoor air introducing port 113. Indoor air (air inside the theater) flows from the indoor air introducing port 112 into the heat exchange chamber 119 and also outdoor air flows from the outdoor air introducing port 113 into the heat exchange chamber 119, and thus the use-side heat exchanger 21 is disposed so that all the indoor air from the indoor air introducing port 112 and the outdoor from the outdoor air introducing port 113 pass through the use-side heat exchanger 21. The use-side heat exchanger 21 is disposed between the two opening portions and the use-side air blower 22 as shown in FIG. 3, and located like a brace.

Furthermore, an opening 118A through which the heat exchanger chamber 119 and the air filtering chamber 120 intercommunicate with each other is formed in the partition plate 118. The use-side air blower 22 is secured at the opening 118A, and air in the heat exchanger 119 is blown through the opening 118A into the air filtering chamber 120 by operating the use-side air blower 22. The air filtering portion 4 is disposed at the downstream side of the use-side air blower 22 in the air filtering chamber 120, and a rear chamber 121 intercommunicating with the air supply duct 105 (FIG. 1) through the air supply port 111 is formed at the downstream side of the air filtering portion 4. Air introduced into the use-side unit 2 is brought into contact with electrolytic water in the air filtering portion 4 to be filtered while passing through the air filtering chamber 120, and the filtered air is passed through the rear chamber 121, the supply port 111 and the air supply duct 105 and then circulated and supplied into the theater 100.

Next, the respective constituent elements of the air filtering unit 150 will be described.

Figure 4:
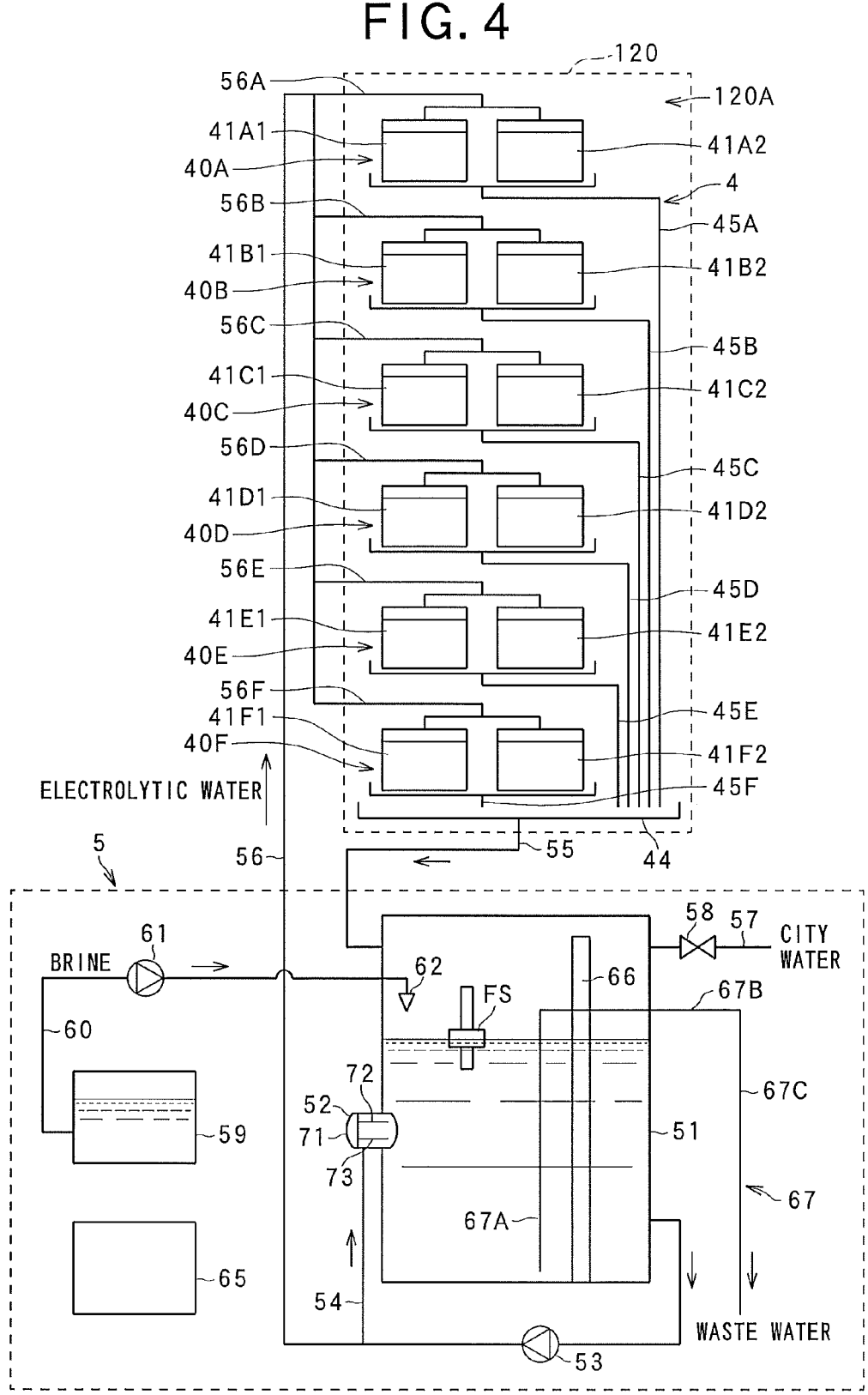
FIG. 4 is a schematic diagram showing circulating flow of electrolytic water in an air filtering unit provided to the air conditioner.

FIG. 4 is a diagram showing the circulating flow of electrolytic water in the air filtering unit 150.

The air filtering unit 150 has the air filtering portion 4 disposed in the air filtering chamber 120, and the electrolytic water circulating and supplying portion 5 disposed so as to be adjacent to the air filtering chamber 120.

The electrolytic water circulating and supplying portion 5 generates electrolytic water having air filtering performance and circulates and supplies the electrolytic water to the air filtering portion 4. The air filtering portion 4 brings air into contact with the electrolytic water supplied from the electrolytic water circulating and supplying portion 5 to filter air.

The air filtering portion 4 has plural (in this embodiment, six) element units 40A, 40B, 40C, 40D 40E and 40F. Each of the element unit comprises a combination of a pair of (two) gas-liquid contact members arranged in a lateral (horizontal) direction substantially over the full width of an air flow passage 120A of the air filtering chamber 120. In this embodiment, totally twenty gas-liquid contact members 41A1 to 41F1, 41A2 to 41F2 are used. The six element units 40A to 40F are stacked at plural (for example, six) stages in the height direction of the air filtering chamber 120 so as to cover substantially the whole cross-sectional area of the air flow passage in the air filtering chamber 120, so that air passing in the air filtering chamber 120 passes through the gas-liquid contact members 41A1 to 41F2 with no leakage.

The gas-liquid contact members 41A1 to 41F2 are members for bringing air passing through the air flow passage 120A into contact with electrolytic water. In these gas-liquid contact members 41A1 to 41F2, air flowing through the air flow passage 120A comes into contact with electrolytic water containing a predetermined active oxygen species, whereby virus, etc. contained in the air are inactivated and thus filtered.

Each of the gas-liquid contact members 41A1 to 41F2 is a filter member having a honeycomb structure or a three-dimensional structure similar to the honeycomb structure, and it is designed so that an element portion with which gas is brought into contact is supported by a frame. The element portion (not shown) is constructed by laminating a corrugated plate member having a corrugated-plate shape and a flat member having a flat-plate shape, and a number of substantially triangular openings are formed between the corrugated plate member and the flat plate member. Accordingly, the gas contact area when air is passed through the element portion is kept to be broad, electrolytic water can be dropped through the element portion, and clogging hardly occurs.

The element portion is formed of an element which is hardly deteriorated by electrolytic water, for example, polyolefin type resin (polyethylene resin, polypropylene resin or the like), PET (polyethylene terephthalate) resin, vinyl chloride resin, fluorinated resin (PTFE, PFA, ETFE or the like), ceramic type material or the like. In this embodiment, PET resin is used. The element portion is subjected to a hydrophilic treatment to enhance affinity to electrolytic water. Accordingly, the water retentivity (wettability) of electrolytic water by the gas-liquid contact members 41A1 to 41F2 is kept, and the contact between active oxygen species (active oxygen material) and air can be kept for a long time.

The number of the gas-liquid contact members is determined in accordance with the amount of air passing through the air filtering chamber 102, and a suitable number can be calculated on the basis of the amount of air passing through the air flow passage 120A and the air filtering performance (gas-liquid contact area) per gas-liquid contact member. Accordingly, the gas-liquid contact members whose number enables sufficient filtering of air are disposed in the air filtering chamber 120. For example, twenty gas-liquid contact members 41A1 to 41F1, 41A2 to 41F2 are used in this embodiment. Furthermore, drain pans 44 for receiving drain discharged from the gas-liquid contact members 41A1 to 41F2 are disposed below the gas-liquid contact members 41A1 to 41F2.

Figure 5:
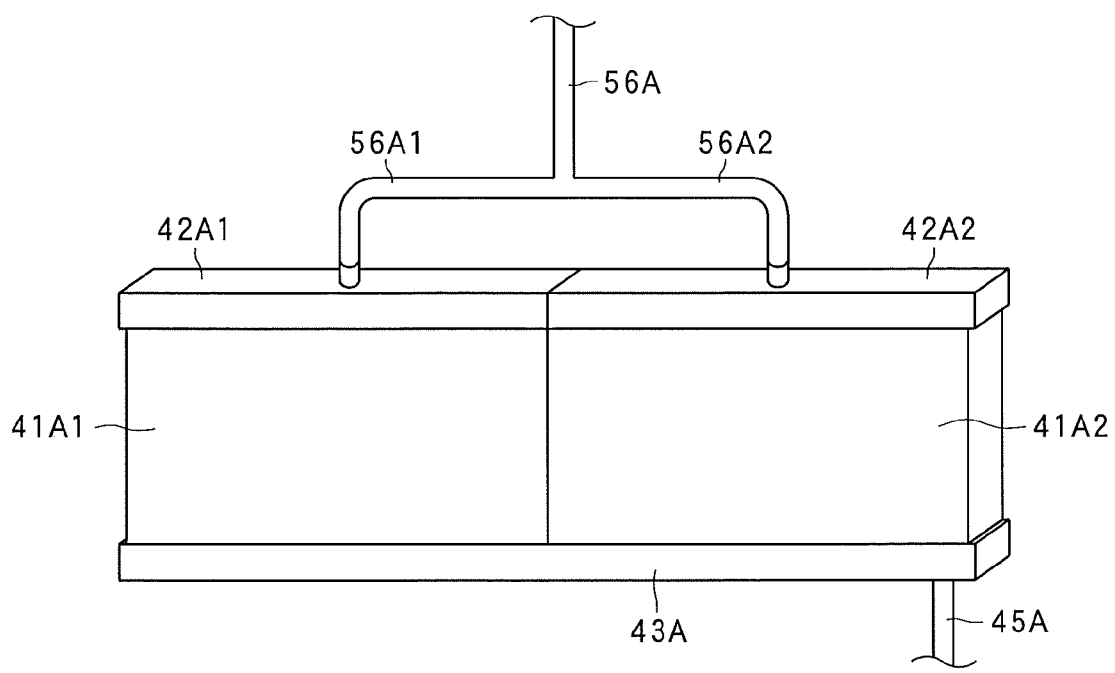
FIG. 5 is a perspective view showing the construction of a gas-liquid contact member.

As shown in FIG. 5, water sprinkling boxes 42A1 and 42A2 for uniformly dispersing electrolytic water to the gas-liquid contact members 41A1 and 41A2 are secured to the upper portions of the gas-liquid contact members 41A1 and 41A2. The water sprinkling box 42A1, 42A2 has a tray member for temporarily stocking electrolytic water, and plural water sprinkle holes (not shown) are formed in the side surfaces of the tray member. Electrolytic water drops through these water sprinkle holes into the gas-liquid contact members 41A1 and 41A2.

Furthermore, a water distributing sheet (not shown) for efficiently dispersing electrolytic water dropping from the water sprinkle box 42A1, 42a2 to the element portion is disposed on the upper surface of the gas-liquid contact member 41A1, 41A2. This water distributing sheet is a sheet formed of textile material (woven fabric, nonwoven cloth or the like) having liquid permeability, and one or plural distributing sheets are provided along the cross-section in the thickness direction.

Furthermore, an electrolytic water tray 43A for receiving water dropping from the gas-liquid contact members 41A1, 41A2 is secured to the lower portion of the gas-liquid contact members 41A1, 41A2. Furthermore, a drain hose 45A for leading water received at the electrolytic water tray 43A to the drain pan 44 (FIG. 4) is secured to the bottom surface of the electrolytic water tray 43A. The gas-liquid contact members disposed at the respective stages have substantially the same construction, and the construction of the gas-liquid contact members 41A1 and 41A2 at the uppermost stage will be described. The constructions of the gas-liquid contact members 41B1, 41B2 to 41F1, 41F2 are represented by the same reference numerals, and the descriptions thereof are omitted.

Next, the arrangement construction of the gas-liquid contact members 41A1, A2 to 41F1, F2 will be described.

Figure 6:
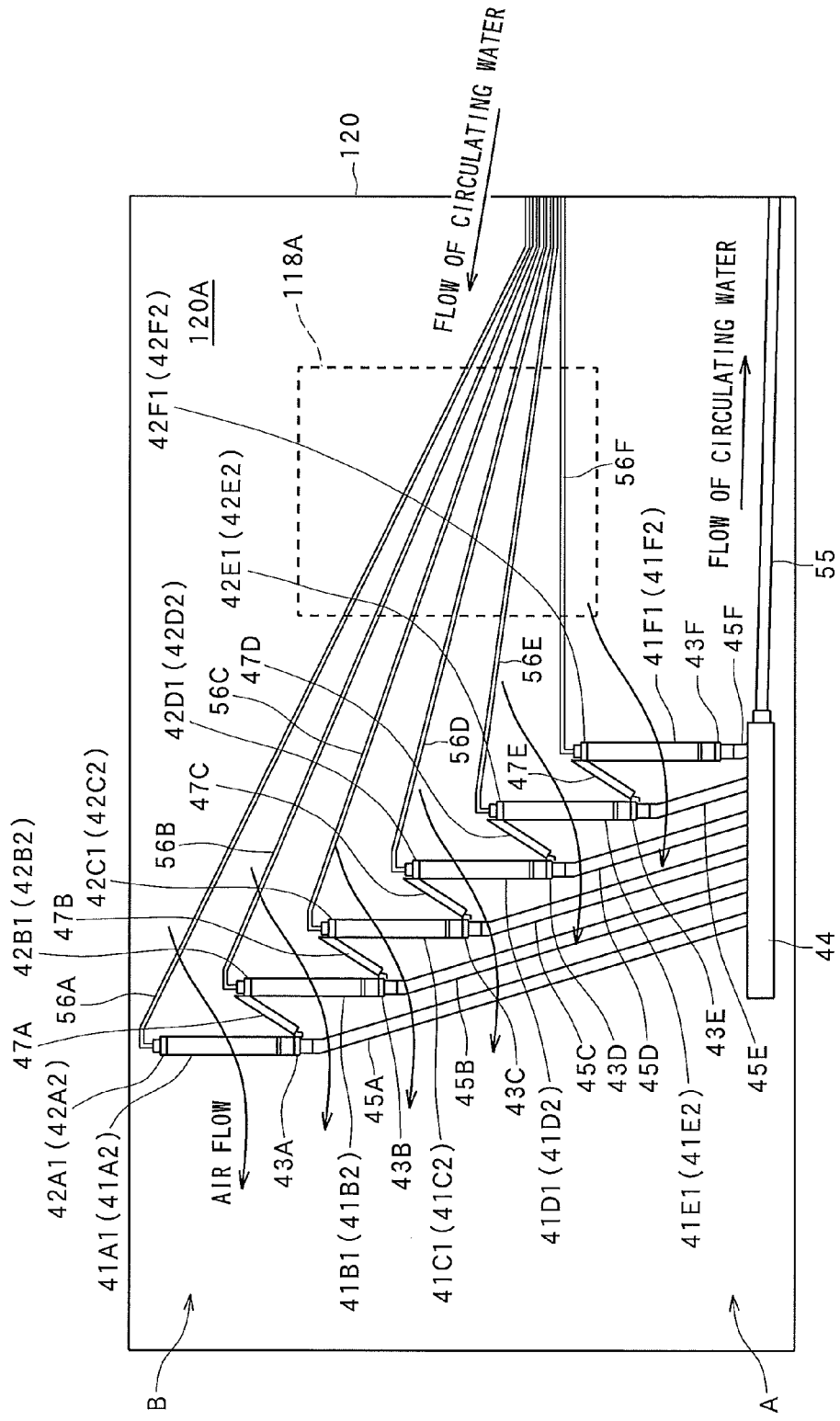
FIG. 6 is a side view showing the arrangement of the gas-liquid contact members.

As shown in FIG. 6, the gas-liquid contact members 41A1, A2 to 41F1, F2 are arranged in the vertical direction (up-and-down direction). The gas-liquid contact members covering a lower area A of the air flow passage 120A (for example, the gas-liquid contact members 41F1, F2) are arranged so as to be successively displaced to the upstream side of the air flow passage 120A with respect to the gas-liquid contact members covering the upper area B (for example, the gas-liquid contact members 41A1, A2).

Furthermore, in this embodiment, the gas-liquid contact members which are adjacent to each other in the air flow direction are arranged so as to be overlapped with each other in the air flow direction (when viewed from the lower side to the upper side in FIG. 3 or viewed from the right side to the left side in FIG. 6), and the gap between the lower end portion of the gas-liquid contact member located at the upper position (for example, the gas-liquid contact members 41A1, A2) and the upper end portion of the gas-liquid contact member which is adjacent to and lower in height than the above gas-liquid contact member and located at the lower position (for example, the gas-liquid contact members 41B1, B2) is closed by an air leading plate 47A to 47E. That is, the lower end of each gas-liquid contact member is connected through the air leading plate to the upper end of the gas-liquid contact member which is adjacent (nearest) to the former gas-liquid contact member and located just at the upstream side of the air flow passage with respect to the former gas-liquid contact member.

In this specification, the "vertical direction" of the arrangement of the gas-liquid contact members may be broadly defined as a direction which is perpendicular or intersects to the air flow direction in the air flow passage 120A.

According to this construction, the plural gas-liquid contact members 41A1, A2 to 41F1, F2 whose total area is larger than the area of the air flow passage 120A can be coherently arranged, whereby the air filtering performance of the gas-liquid contact members 41A1, A2 to 41F1, F2 arranged in the air flow passage 120A can be enhanced. Furthermore, the lower end portion of the gas-liquid contact member located at the upper portion and the upper end portion of the gas-liquid contact member which is nearest to the above gas-liquid contact member and located at the lower portion is closed by the air leading plate, so that air can be prevented from flowing into the air flow passage 120A without passing through the gas-liquid contact members 41A1, A2 to 41F1, F2. Here, the plural gas-liquid contact members 41A1 to 41F2 and the air leading plates 47A to 47E may be arranged so as to form a corrugated (undular or wiggly) arrangement in side view while displaced from one another in a direction perpendicular or intersecting to the air flow direction as a whole as shown in side view of FIG. 6).

Furthermore, as shown in FIG. 4, the electrolytic water circulating and supplying portion 5 as an electrolytic water generating device has a water stock tank 51 (water tank), an electrolytic unit 52 for electrolyzing water in the water stock tank 51 to generate electrolytic water, an electrolytic water supply pipe (supply pipe) 56 for supplying the electrolytic water in the water stock tank 51 to the respective gas-liquid contact members 41A1, A2 to 41F1, F2 of the air filtering portion 4, a water feeding pump 53 provided to the electrolytic water supply pipe 56, a branch pipe 54 which is branched from the electrolytic water supply pipe 56 at the downstream side of the water feeding pump 53 and connected to the electrolytic unit 52, a circulating water return pipe 55 for leading water dropping onto the drain pan 44 to the water stock tank 51, and a controller 65 for controlling the operation of the electrolytic unit 52, the water feeding pump 53, etc.

A water supply pipe 57 for supplying city water (tap water) or the like into the water stock tank 51 and a water supply valve 58 are connected to the water stock tank 51, and the water supply valve 58 is controlled to open/close on the basis of the operation of a float switch FS provided in the water stock tank 51 under the control of the controller 65. Here, a water supply source which is connected to the water supply pipe 57 and supplies water to the water stock tank 51 may be city water (tap water), or water or the like stocked in a water supply tank or the like. The water stocked in the water supply tank or the like may be water containing ion species such as chloride ions such as tap water or the like in advance, or well water or the like. When water containing a rare concentration of chloride ions or the like well water or the like is used, chloride ions may be added to this water to adjust the concentration of the chloride ions to the same level as tap water. In this embodiment, these kinds of water is referred to as "water".

In this construction, when water containing a rare concentration of chloride ions such as well water or the like is used, a brine tank 59 for stocking brine whose concentration is adjusted to a predetermined value in advance may be provided to add chloride ions to the water concerned. A brine supply pump 61 is connected through a brine supply pipe 60 to the brine tank 59, and brine in the brine tank 59 is supplied into the water stock tank 51 by the brine supply pump 61. Furthermore, a check valve 62 is provided to the brine supply pipe 60 connected to the water stock tank 51. The brine supply pump 61 may be designed to be operated under the control of the controller 65 on the basis of the electric conductivity detected by the electrolytic unit 52.

In order to efficiently generate active oxygen species, the electrolyte to be added to water in the water stock tank 51 is not limited to salt, and it may be another electrolyte. For example, calcium chloride or magnesium chloride may be used, or haloid salt containing another halogen or various kinds of salt of halogen acid containing chlorine and other halogen may be used. Furthermore, electrolyte containing no halogen may be used. These electrolytes are preferably soluble in water.

Furthermore, in this embodiment, the electrolytic water supply pipe 56 connected to the connection port of the water stock tank 51 is branched to six electrolytic water supply pipes 56A to 56F, and electrolytic water fed from the water feeding pump 53 is substantially equally distributed to the electrolytic water supply pipes 56A to 56F.

Furthermore, as shown in FIG. 5, the electrolytic water supply pipe 56A is branched to two branch pipes 56A1 and 56A2 at the end portion of the downstream side, and these branch pipes 56A1, 56A2 are connected to the water sprinkle boxes 42A1, 42A2 of the gas-liquid contact members 41A1, 41A2 to supply electrolytic water through these sprinkle boxes 42A1, 42A2 into the gas-liquid contact members 41A1, 41A2. The other electrolytic water supply pipes 56B to 56F have the same construction, whereby electrolytic water is supplied to the respective element units 40A to 40F.

The electrolytic water supplied to the electrolytic water supply pipes 56A to 56F infiltrates into the gas-liquid contact members 41A1 to 41F2, and drops from the gas-liquid contact members 41A1 to 41F2. The dropping electrolytic water is collected at the drain pan 44, and returned through the circulating water return pipe 49 into the water stock tank 51.

The electrolytic unit 52 is fixedly disposed on the side surface of the water stock tank 51. Specifically, the electrolytic unit 52 has a cylindrical case body 71 having a bottom surface, and at least a pair of electrode plates 72 and 73 accommodated in the case body 71. By applying a voltage between the electrode plates 72 and 73, water is electrolyzed to generate electrolytic water containing active oxygen species.

Here, the active oxygen species is oxygen molecules having higher oxidizing activity than normal oxygen and relevant materials thereto, and contain not only so-called narrowly-defined active oxygen such as superoxide anion, singlet oxygen, hydroxyl radical and hydrogen peroxide, but also so-called broadly-defined active oxygen such as ozone, hypochlorous acid, hypohalous acid, etc.

The electrode plates 72, 73 are constructed by two electrode plates each of which comprises a base of Ti (titan) and a coated layer of Ir (iridium) and a coated later containing Pt (platinum).

By applying a voltage between the electrodes 72 and 73, the following reaction (formula (1)) occurs at the cathode:

$$2H_2O + 2e^- \rightarrow H_2 + 2OH^- \tag{1}$$

Furthermore, the following reaction (formula (2)) occurs at the anode:

$$2H_2O \rightarrow O_2 + 4H^+ + 4e^- \tag{2}$$

By combining these reactions at the cathode and the anode, water is electrolyzed according to the following formula (3):

$$2H_2O \rightarrow 2H_2 + O_2 \tag{3}$$

In addition to this reaction, chlorine ions contained water (chloride ions: Cl⁻) react according to the following formula (4), and chlorine ($Cl_2$) occurs:

$$2Cl^- \rightarrow Cl_2 + 2e^- \tag{4}$$

Furthermore, $Cl_2$ thus generated reacts with water according to the following formula (5), and hypochlorous acid (HClO) and hydrogen chloride (HCl) occur:

$$Cl_2 + H_2O \rightarrow HClO + HCl \tag{5}$$

Hypochlorous acid occurring at the anode has strong oxidizing action and a bleaching action. Water solution in which hypochlorous acid is dissolved, that is, electrolytic water generated in the electrolytic unit 52 exercises various kinds of air cleaning effects such as inactivation of virus, etc., sterilization, decomposition of organic compounds, etc. When electrolytic water containing hypochlorous acid flows through the electrolytic water supply pipes 56A to 56F, and is dropped through the water sprinkle boxes 42A1, 42A2 to 42F1, 42F2 to the gas-liquid contact members 41A1, 41A2 to 41F1, 41F2, air blown out from the use-side air blower 22 is brought into contact with hypochlorous acid in the gas-liquid contact members 41A1, 41A2 to 41F1, 41F2. Accordingly, virus, etc. floating in the air are inactivated, and also odor materials contained in the air concerned react with hypochlorous acid to be decomposed or ionized, so that the order materials are dissolved in the water. Accordingly, air filtering and deodorization are performed, and cleaned air is discharged from the gas-liquid contact members 41A1, 41A2 to 41F1, 41F2.

An inactivating mechanism of virus, etc. by the active oxygen species will be described by exemplifying influenza virus. The active oxygen species functions to break down and vanish (remove) the surface protein (spike) of the virus concerned which is indispensable for infection. When the surface protein of influenza virus is broken down, the influenza virus is not joined to a receptor which is necessary for infection of the virus concerned, so that infection can be prevented. Therefore, influenza virus floating in the air is brought into contact with the electrolytic water containing the active oxygen species in the gas-liquid contact members 41A1, 41A2 to 41F1, 41F2, so that the influenza virus loses so-called infection power, and thus the infection can be prevented.

Accordingly, by disposing the gas-liquid contact members 41A1, A2 to 41F1, F2 in the air filtering chamber 120 of the rooftop type air conditioner 110, air passing through the air filtering chamber 120 is filtered in the gas-liquid contact members 41A1, A2 to 41F1, F2, and the filtered air concerned can sufficiently pervade the inside of the theater 100, so that air filtering and deodorization in the large-space facilities can be easily and efficiently performed.

Here, an electrode switching operation of applying positive potential to any one side of the electrode plates 72 and 73 in the electrolytic unit 52 can be performed by inverting the polarities of the electrodes. In this embodiment, this operation can be performed by changing (inverting) the voltage applied between the electrode plates 72 and 73 under the control of the controller 65.

Furthermore, the concentration of the active oxygen species in the electrolytic water is adjusted to such a concentration that virus, etc. to be filtered can be inactivated under the control of the controller 65. The adjustment of the concentration of the active oxygen species is performed by adjusting the voltage applied between the electrode plates 72 and 73 to adjust a current value flowing between the electrode plates 72 and 73.

For example, when the electrode plate 72 is supplied with positive potential and the current value flowing between the electrode plates 72 and 73 is set to 20 mA (milliampere)/cm$^2$ (square centimeter) in current density, a predetermined free residual chlorine concentration (for example, 1 mg (milligram)/1 (liter) occurs. The concentration of the hypochlorous acid in electrolytic water can be adjusted to a high concentration by changing the voltage applied between the electrode plates 72 and 73 to increase the current value.

Next, the fixing structure of the electrolytic water 52 will be described.

Figure 7:
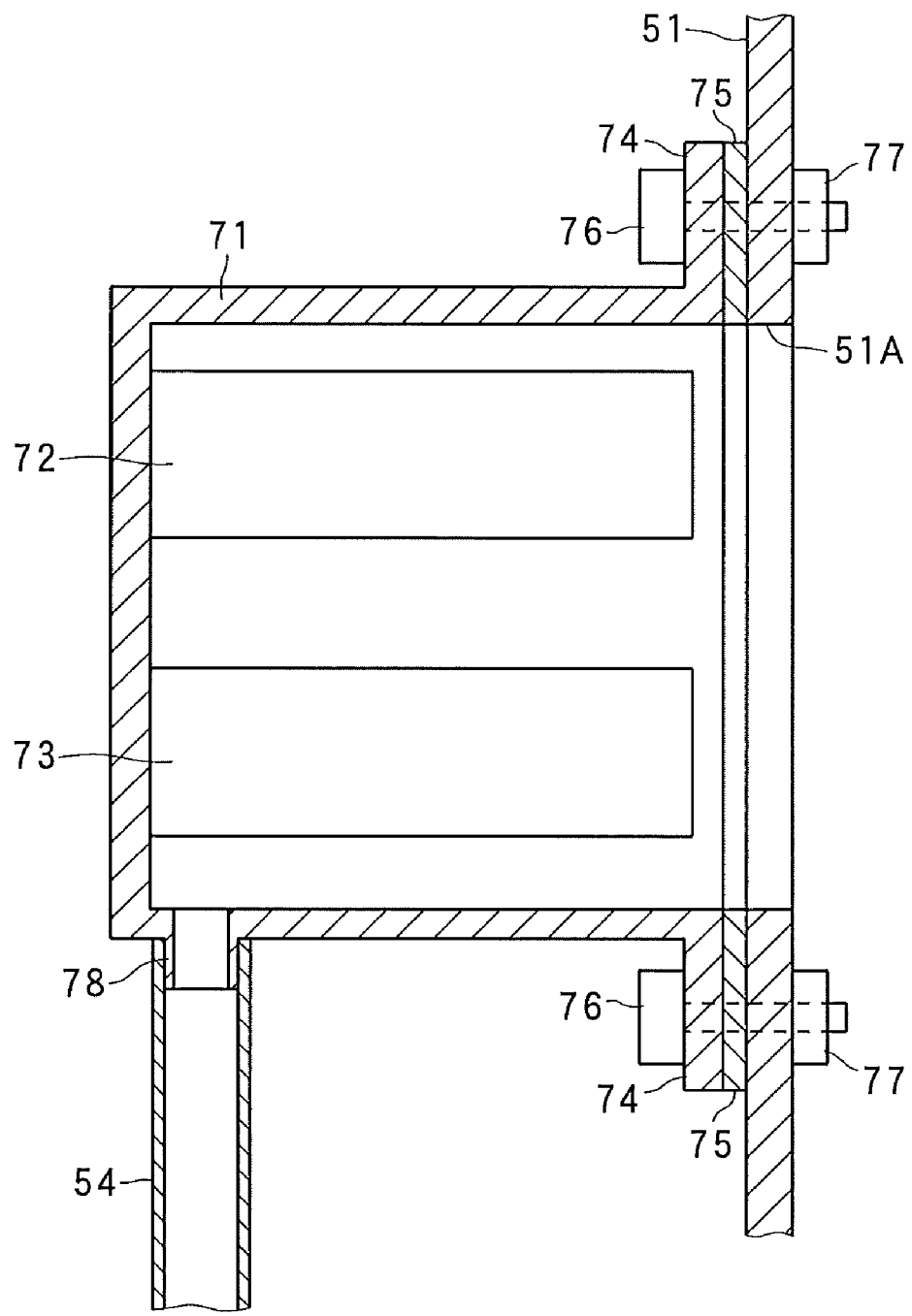
FIG. 7 is a diagram showing a fixing structure of an electrolytic unit.

As shown in FIG. 7, the case body 71 of the electrolytic unit 52 has a flange 74 formed around an opening thereof, and this flange 74 is fixed to an opening portion 51A formed in the side surface of the water stock tank 51 through a packing 75 by bolts 76 and nuts 77.

This opening portion 51A is formed to have substantially the same diameter as the case body 71, and the electrodes 72 and 73 in the case body 71 can be accessed from the inside of the water stock tank 51 through the opening portion 51A. Therefore, even when materials contained in water in the electrolysis process adhere to the electrodes 72 and 73 as scale type materials, the work of removing the scale type materials concerned can be easily performed through the opening portion 51A of the water stock tank 51.

Furthermore, a connection port 78 is formed in the bottom surface at a side far away from the flange 74, and the branch pipe 54 is connected to this connection port 78. As described above, in this construction, the branch pipe 54 which is branched from the electrolytic water supply pipe 56 at the downstream side of the water feeding pump 53 and connected to the electrolytic unit 52 is provided, a part of electrolytic water in the water stock tank 51 which is sucked by the water feeding pump 53 and supplied through the electrolytic water supply pipe 56 to the plural gas-liquid contact members 41A1, A2 to 41F1, F2 is led to the electrolytic unit 52 to generate electrolytic water in the electrolytic unit 52, and the generated electrolytic water is returned into the water stock tank 51. Therefore, the variation width of the electrolytic water concentration in the water stock tank 51 can be suppressed to a small value, and a stable concentration of electrolytic water can be supplied to the gas-liquid contact members 41A1, A2 to 41F1, F2. Therefore, the air filtering operation in each of the gas-liquid contact members 41A1, A2 to 41F1, F2 can be stably performed. Therefore, a large amount of air to be supplied into the theater 100 through the air blow-out ports 104 can be uniformly filtered.

Furthermore, according to this construction, when scale type materials occurring on the electrodes 72 and 73 are removed from the electrodes 72 and 73, these scale type materials are returned to the water stock tank 51 together with the electrolytic water, and deposited in the water stock tank 51. Therefore, the scale type materials are prevented from flow to the gas-liquid contact members 41A1, A2 to 41F1, F2 through the electrolytic water supply pipe 56. Therefore, blockage of the electrolytic water supply pipe 56 due to flow-in of the scale type materials or clogging of the gas-liquid contact members 41A1, A2 to 41F1, F2 can be prevented. Therefore, the maintenance frequency of the electrolytic water supply pipe 56 and the gas-liquid contact members 41A1, A2 to 41F1, F2 can be reduced, and the maintenance work can be alleviated.

Furthermore, in this construction, as shown in FIG. 4, a scale filter 66 for compartmenting the inside of the water stock tank 51 is provided between the opening portion 51A of the water stock tank 51 to which the electrolytic unit 52 is directly secured, and the connection port 51B to which the electrolytic water supply pipe 56 is connected. Therefore, scale type materials deposited in the water stock tank 51 are collected by this scale filter 66, and thus these scale type materials are prevented from flowing out to the outside of the water stock tank 51.

Furthermore, the water stock tank 51 is provide with a waste water pipe (drain pipe) 67 for discharging water in the water stock tank 51 in a siphon manner. The waste water pipe 67 has a first vertical portion 67A extending from the bottom portion of the water stock tank 51 upwardly, a horizontal portion 67B intercommunicating with the first vertical portion 67A and extending substantially horizontally, and a second vertical portion 67C intercommunicating with the horizontal portion 67B and extending downwardly at the outside of the tank. The horizontal portion 67B is located at a slightly higher position than the normal controlled water level in the water stock tank 51. Water is supplied by opening the water supply valve 58 until the water level reaches this height position, whereby water in the water stock tank 51 is discharged by the siphon principle. In this construction, an exhaust valve is not required, so that the cost can be reduced and also the water waste speed can be enhanced by the siphon system.

As described above, according to this embodiment, the air conditioner 110 which is connected through the air supply duct 105 to the plural air blow-out ports 104 opened to the inside of the theater 100 as a large space and supplies the air-conditioned air through the air supply duct 105 into the inside of the theater 100 is provided, the air filtering chamber 120 is provided in the air flow passage extending from the air conditioner 110 to the plural air blow-out ports 104, and the air filtering portion 4 having the plural gas-liquid contact members 41A1, A2 to 41F1, F2 for filtering the air-conditioned air by bringing the air-conditioned air into contact with electrolytic water is provided in the air filtering chamber 120. Therefore, the air filtered in the gas-liquid contact members 41A1, A2 to 41F1, F2 is supplied through the air supply duct 105 to the air blow-out ports 104, and the filtered air is made to pervade the inside of the theater 100 through the air blow-out ports 104, whereby the air supplied to the theater 100 can be filtered with a simple construction. Furthermore, the gas-liquid contact members 41A1, A2 to 41F1, F2 are provided so as to concentrate in the air filtering chamber 120, and thus the maintenance of the gas-liquid contact members 41A1, A2 to 41F1, F2 can be easily performed.

Furthermore, the water stock tank 51 connected through the water feeding pump 53 to the electrolytic water supply pipe 56 for supplying electrolytic water to the gas-liquid contact members 41A1, A2 to 41F1, F2 is provided, the electrolytic unit 52 for generating electrolytic water is provided, and the mechanism for leading to the electrolytic unit 52 a part of electrolytic water in the water stock tank 51 which is sucked by the water feeding pump 53 and supplied through the electrolytic water supply pipe 56 to the plural gas-liquid contact members 41A1, A2 to 41F1, F2, generating electrolytic water in the electrolytic unit 521 and returning the generated electrolytic water into the water stock tank 51 is provided. Therefore, the variation width of the electrolytic water concentration in the water stock tank 51 can be suppressed to be small, and a stable concentration of electrolytic water can be supplied to the respective gas-liquid contact members 41A1, A2 to 41F1, F2. Therefore, the air filtering in each of the gas-liquid contact members 41A1, A2 to 41F1, F2 can be stably performed, and thus a large amount of air supplied to the theater 100 through the air blow-out ports 104 can be uniformly filtered.

Furthermore, according to this embodiment, the electrolytic unit for generating electrolytic water is directly secured to the water stock tank 51, and scale type materials generated in the electrolytic unit 52 are returned into the water stock tank 51 together with the electrolytic water. Therefore, scale type materials generated in the electrolytic unit 52 in the electrolysis process are returned into the water stock tank 51 together with the electrolytic water, and deposited in the water stock tank 51. Therefore, the scale type materials are prevented from flowing into the gas-liquid contact members 41A1, A2 to 41F1, F2 through the electrolytic water supply pipe 56. Therefore, blockage of the electrolytic water supply pipe due to flow-in of the scale type materials and clogging of the gas-liquid contact members 41A1, A2 to 41F1, F2 are prevented, so that the maintenance frequency of the electrolytic water supply pipe 56 and the gas-liquid contact members 41A1, A2 to 41F1, F2 is reduced and thus the maintenance work can be lightened.

Furthermore, according to this embodiment, the air conditioner 10 is designed so that the inside of the housing 114 thereof id divided into three chambers. The first chamber is used as the heat exchange chamber 119 in which the use-side heat exchanger 21 and the use-side air blower 22 are mounted, the second chamber is used as the machine chamber 116 in which the compressor 11 is mounted, and the third chamber is used as the air filtering chamber 120 through which the air-conditioned air from the heat-exchanger chamber 119 is circulated. Therefore, the air filtering portion 4 can be easily disposed in the air filtering chamber 120 formed in the housing 114 of the air conditioner 110. Therefore, a large amount of air-conditioned air to be supplied to the theater 100 (large space) can be filtered without jumboizing the apparatus, but with a simple construction.

Still furthermore, according to this embodiment, the plural gas-liquid contact members 41A1, A2 to 41F1, F2 are arranged so as to cover substantially the whole cross-sectional area of the air flow passage 120A of the air filtering chamber 120. Therefore, air passing through the air flow passage 120A in the air filtering chamber 120 is uniformly filtered by the gas-liquid contact members 41A1, A2 to 41F1, F2, and thus a large amount of air-conditioned air to be supplied into the theater 100 through the air blow-out ports 104 can be uniformly filtered.

Furthermore, the gas-liquid contact members 41A1, A2 to 41F1, F2 are arranged in the vertical direction, and the gas-liquid contact members covering the lower area A of the air flow passage 120A are arranged so as to be successively displaced from the gas-liquid contact members covering the upper area B to the upstream side of the air flow passage 120A. Therefore, the gas-liquid contact members 41A1, A2 to 41F1, F2 whose total area is larger than the opening area (the area of the cross-sectional area) of the air flow passage 120A can be coherently arranged, so that the air filtering performance of the gas-liquid contact members 41A1, A2 to 41F1, F2 arranged in the air flow passage 120A can be enhanced.

In this embodiment, the water circulation system in which water received by the drain pan 44 is returned through the circulating water return pipe 55 to the water stock tank 51 is adopted as described above, and the air filter can be efficiently performed for a long time by effectively using a small amount of water. Furthermore, the water level in the water stock tank 51 is reduced due to evaporation. Therefore, the water supply valve 58 is opened through the operation of the float switch FS, and thus a proper amount of tap water is supplied from the water supply port. As described above, the consumption amount of water can be reduced as compared with a system of directly discharging water received by the drain pan 44, and the running cost when the air filtering unit 150 is operated can be reduced.

Particularly, with respect to the rooftop type air conditioner 110 according to this embodiment, the amount of air to be fed into a building 200 is large, and thus the amount of water to be supplied to the gas-liquid contact members 41A1, A2 to 41F1, F2 to filter this air is increased in accordance with the air amount. Accordingly, a water saving effect obtained by returning water received at the drain pan 44 through the circulating water return pipe 55 to the water stock tank 51 in the rooftop type air conditioner 110 is very higher.

Next, the construction of the electrolytic water circulating and supplying portion 5 will be described in detail.

Figure 8:
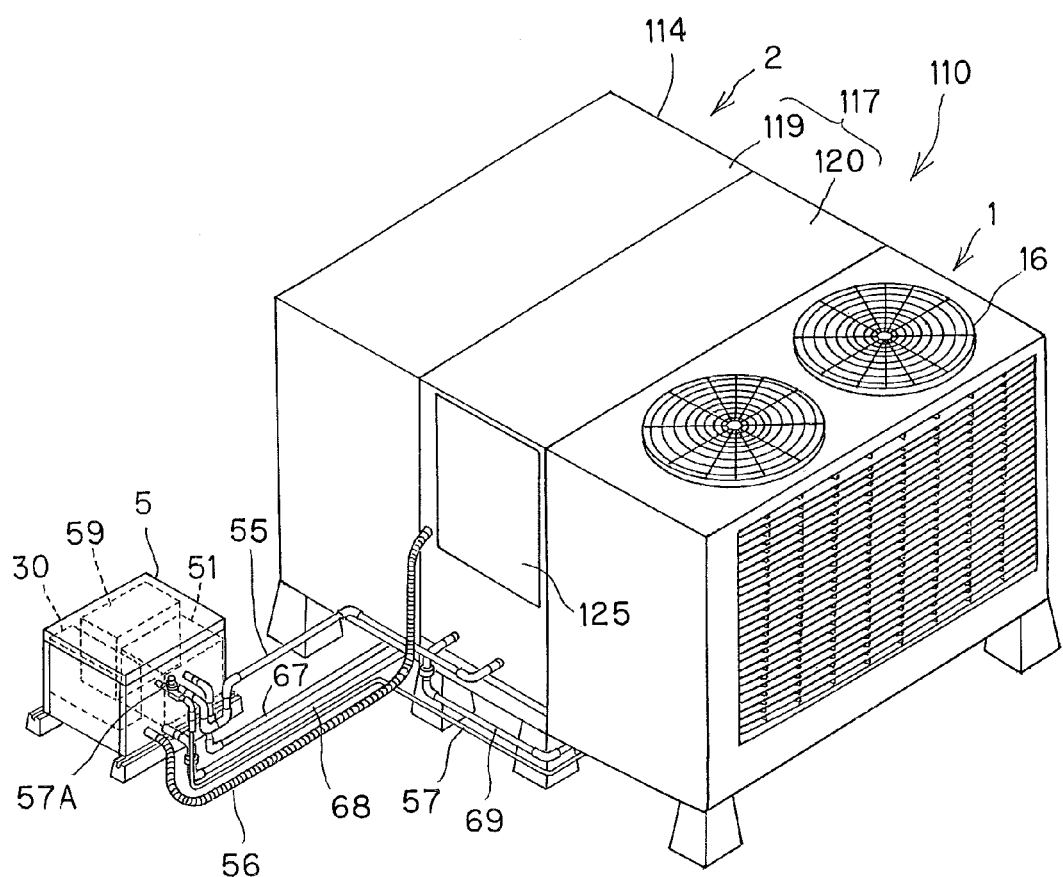
FIG. 8 is a diagram showing the construction and arrangement state of an electrolytic circulating and supply unit.

FIG. 8 is an outlook perspective view showing the construction and installation state of the electrolytic water circulating and supplying portion 5. In order to make the understanding more easy, the heat-source side unit 1, the use-side unit 2 and the electrolytic water circulating and supplying portion 5 are illustrates together with a wire group laid between the heat-source side unit 1 and the use-side unit 2.

As shown in FIG. 8, the electrolytic water circulating and supplying portion 5 has a case 50 constructed as an unit separate from the heat-source side unit 1 and the use-side unit 2, and the water stock tank 51 (water tank), the brine tank 59 (water solution tank) and an electrical component box 30 are accommodated in the case 50. The electrolytic water supply pipe 56 for supplying electrolytic water from the electrolytic water circulating and supplying portion 5 to the air filtering chamber 120 and the circulating water return pipe 55 for circulating electrolytic water from the air filtering chamber 120 to the electrolytic water circulating and supplying unit 5 are connected between the electrolytic water circulating and supplying unit 5 and the air filtering chamber 120.

Furthermore, the water supply pipe 57 for supplying city water to the electrolytic water circulating and supplying portion 5 is connected through a pressure-reducing valve 57A to the electrolytic water circulating and supplying portion 5. An overflow pipe 68 for exhausting water when the water level in the water stock tank 51 exceeds a predetermined water level, and the drain pipe 67 for discharging electrolytic water in the water stock tank 51 are secured to the electrolytic water circulating and supplying portion 5.

Still furthermore, a drain pipe 69 for discharging electrolytic water from the air filtering unit 150 mounted in the air filtering chamber 120 to the outside of the air conditioner 110 is connected to the air filtering chamber 120.

The water stock tank 51 is disposed in the electrolytic water circulating and supplying portion 5 so as to be located at a side nearer to the air filtering chamber 120, and the brine tank 59 is disposed so as to be adjacent to and juxtaposed with the water stock tank 51, and the electrical component box 30 is disposed at the opposite side to the air filtering chamber 120.

Figure 9:
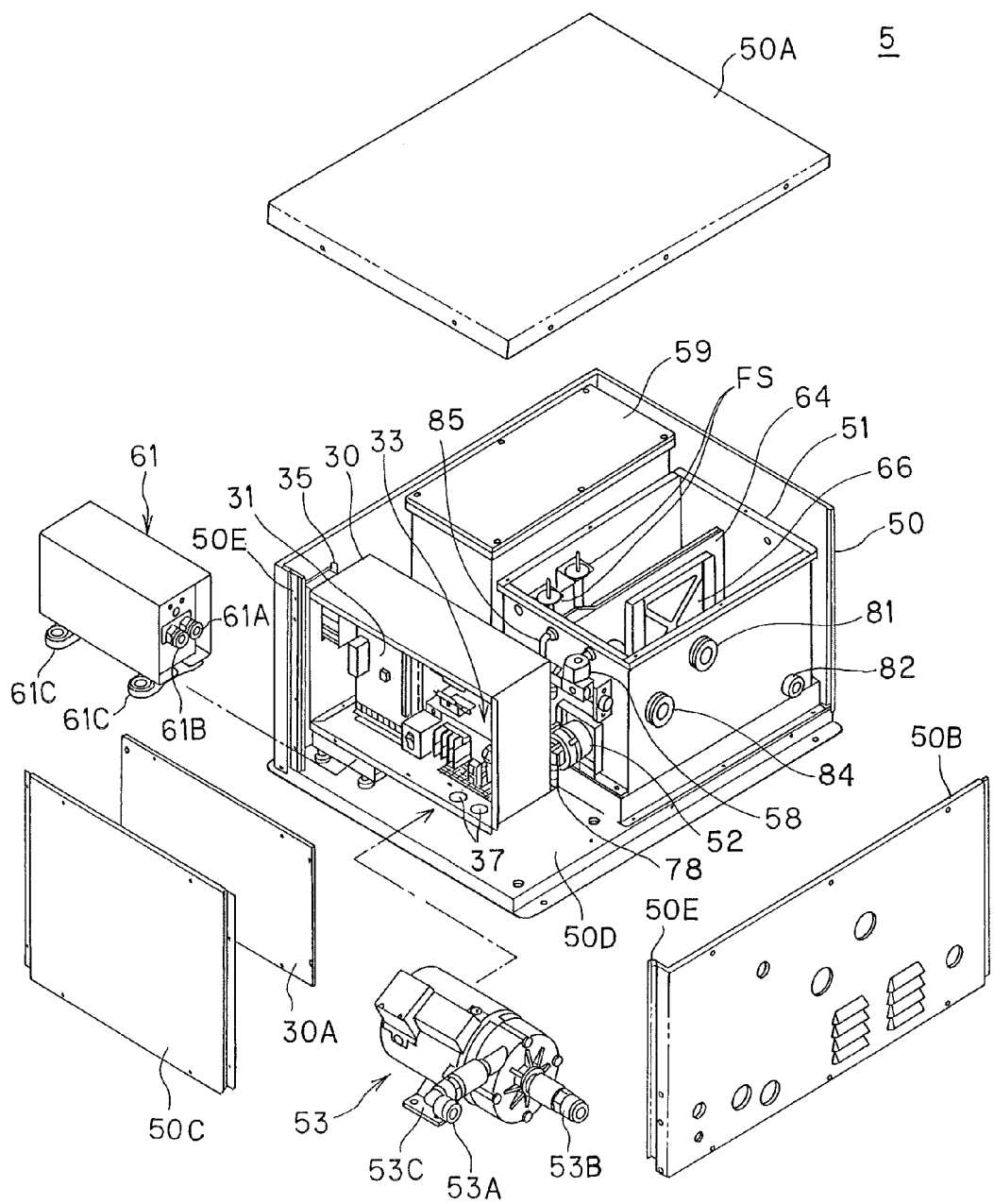
FIG. 9 is an exploded perspective view showing the construction of the electrolytic water circulating and supplying unit.

FIG. 9 is an exploded perspective view showing the construction of the electrolytic water circulating and supplying portion 5.

As shown in FIG. 9, the case 50 of the electrolytic water circulating and supplying portion 5 has a rectangular parallelepiped shape. The upper surface of the case 50 serves as a detachable lid 50A, and two surfaces of the other side surfaces serve as a detachable pipe lead-out panel 50B and an electrical component box side panel 50C. The other side surfaces and the bottom surface 50B are integrally joined to one another.

The pipe lead-out panel 50B corresponds to the side surface at which the water stock tank 51 is disposed, and plural holes through which various kinds of pipes intercommunicating with the outside of the electrolytic water circulating and supplying portion 5 and the water stock tank 51 are formed in the pipe lead-out panel 50B. The electrical component box side panel 50C corresponds to the side surface at the opposite side to the air filtering chamber 120 (FIG. 8), and it is fixed to the pipe lead-out panel 50B and a cover fixing portion 50E formed on the surface confronting the pipe lead-out panel 50B by screws.

The lid 50A is fixed by screws or the like (not shown), and it is opened by detaching the screws. Under the open state of the lid 50A, the respective elements such as the electrical component box 30, the water stock tank 51, the water feeding pump 53, the brine tank 59, the supply pump 61, etc. which are mounted in the case 50 can accessed.

The lid 50A covers the upper surface of the case 50 and the upper end of each side surface of the case 50 in order to prevent invasion of rain water and dust into electrolytic water circulating and supplying portion 5 which is set outdoors. Therefore, when the pipe lead-out panel 50B and the electrical component box side panel 50C are detached, the lid 50A is first detached. When the lid 50A is detached, the electrical component box side panel 50C is first allowed to be detached. When the electrical component box side panel 50C is detached, the pipe lead-out panel 50B is allowed to be detached.

When the electrical component box side panel 50C (service panel) is detached, one side surface of the case 50 is released, and the electrical component box cover 30A (cover) constituting one side surface of the electrical component box 30 of the rectangular parallelepiped is exposed, so that the electrical component box cover 30A is enabled to be detached to the electrical component box side panel 50C side. In the electrical component box 30 are mounted a control board 31 having a microcomputer constituting the controller 65 (FIG. 4), etc. mounted thereon, a power supply circuit portion (electrical circuit portion) 33 for supplying power to the electrolytic unit 52, the water feeding pump 53, the water feeding pump 53, the supply pump 61, etc., etc. When the electrical component box cover 30A is detached, one side surface of the electrical component box 30 is released, and the control board 31, the power supply circuit portion 33, etc. mounted in the electrical component box 30 can be accessed.

As described above, when the lid 50A is detached and the electrical component box side panel 50C is detached, the electrical component box cover 30A is exposed, and thus the inside of the electrical component box 30 can be accessed by detaching the electrical component box cover 30A. Accordingly, the maintenance of the electrical component box 30 can be remarkably easily performed.

In the case 50, the water stock tank 51 and the brine tank 59 are arranged in juxtaposition with each other and the electrical component box 30 having a longitudinal box shape is disposed along the arrangement direction of the water stock tank 51 and the brine tank 59.

The electrical component box 30 is fixed to the side surface of the case 50 through a bracket 35 so that the bottom surface thereof is floated from the bottom surface 50D of the case 50. The supply pump 61 (the water solution supply pump) and the water feeding pump 53 (electrolytic water supply pump) are disposed in juxtaposition with each other in the space below the electrical component box 30. The supply pump 61 is located at the brine tank 59 side, and the water feeding pump 53 is located at the water stock tank 51 side.

Here, the electrical component box 30 is fixed so as to be floated from the bottom surface 50D. Therefore, water, electrolytic water or brine which leaks or overflows from each portion in the case 50 is prevented from invading into the inside of the electrical component box 30, and the control board 31 and the power supply circuit portion 33 can be surely protected. Accordingly, the power supply circuit portion 33, etc. can be mounted in the same case 50 as the water stock tank 51 and the brine tank 59.

The supply pump has a suction port 61A connected to the inside of the brine tank 59 through the brine water supply pipe 60 and a discharge port 61 connected to a brine water pouring portion 85 of the water stock tank 51, and discharges brine sucked from the suction port 61A through the discharge port 61B. The leg portions 61C of the supply pump 61 are fixed to the bottom surface 50D. The water feeding pump 53 has a suction port 53A for sucking electrolytic water in the water stock tank 51, and a discharge port 53B for discharging electrolytic water sucked from the suction port 53A to the water feeding pump 53. Here, a part of electrolytic water discharged from the discharge port 53B is supplied to the electrolytic unit 52 as described later. The leg portions 53C of the water feeding pump 53 is fixed to the bottom surface 50D.

The electrolytic unit 52 is fixed to a surface of the water stock tank 51 which faces the electrical component box 30, and also the brine water pouring portion 85 to which the brine fed out from the supply pump 61 is poured and an electrolytic water supply port 88 for supplying electrolytic water in the water stock tank 51 are disposed on the surface concerned. Accordingly, at the lower side of the electrical component box 30, the supply pump 61 is disposed at the brine tank 59 side and the water feeding pump 53 is disposed at the water stock tank 51 side, whereby the length of the pipe laid between each tank and each pump may be short, and thus lean piping can be performed.

Specifically, all the respective pipes of the branch pipe 54, the electrolytic water supply pipe 56, the brine supply pipe 60 and the drain pipe 67 shown in FIG. 4 are laid below the electrical component box 30 or between the electrical component box 30 and each of the water stock tank 51 and the brine tank 59. Therefore, the lengths of the pipes can be reduced and the pipes are concentrated, so that the maintenance can be easily performed.

Furthermore, wires extending from the power supply circuit portion 33 are connected through a wire penetrating hole 37 formed in the bottom surface of the electrical component box 30 to the supply pump 61 and the water feeding pump 53 disposed below the electrical component box 30. Therefore, the lengths of wires between the power supply circuit portion 33 and each of the supply pump 61 and water feeding pump 53 may be short, and thus the layout of wires can be facilitated.

Still furthermore, the power supply circuit portion 33 is disposed at a position nearer to the water stock tank 51 in the electrical component box 30, and the control board 31 is disposed at a position farther from the water stock tank 51 in the electrical component box 30.

On the control board 31 is mounted the controller 65 (FIG. 4) for controlling the electrolytic unit 52, the water feeding pump 53, the water supply valve 58, the supply pump 61, etc. on the basis of detection values of the float switch FS, etc. described later. Accordingly, the control board 31 is connected to the respective units (portions) by wires. The power supply circuit portion 33 supplies driving current for operating the electrolytic unit 52, the water feeding pump 53 and the supply pump 61 according to the control of the controller 65. Therefore, the current output from the power supply circuit portion 33 is larger than that of the control board 31, and the wires to be connected to the power supply circuit portion 33 are adapted to large current. Therefore, the wires extending from the power supply circuit portion 33 to the respective portions are thicker than the wires extending from the control board 31 to the respective portions. Therefore, the layout of the former wires is difficult and these wires are generally high in price. Therefore, by disposing the power supply circuit portion 33 at the water stock tank 51 side, the lengths of the wires extending from the power supply circuit portion 33 to the electrolytic unit 52 and the water feeding unit 53 can be shortened, the layout of the wires can be facilitated, and the cost can be reduced.

As shown in FIG. 9, the water stock tank 51 has no lid, and the inside of the water stock tank 51 is exposed when the lid 50A of the case 50 is opened. Therefore, by merely opening the lid 50A, maintenance such as removal of scale accumulated in the water stock tank 51, etc. can be simply performed.

Furthermore, the surface of the water stock tank 51 at the pipe lead-out panel 50B side is provided with an overflow discharge port 81, a drip hole 82 and a circulating water return port 84. The overflow discharge port 82 is an opening portion for discharging electrolytic water to the overflow pipe 68 (FIG. 8) when the water level of electrolytic water in the water stock tank 51 exceeds the height of the overflow discharge port 81. The circulating water return port 84 is an opening portion to which the circulating water return pipe 55 from the air filtering chamber 120 is connected. The drip hole 82 is an opening portion for forcedly discharging all the amount of electrolytic water in the water stock tank 51 under the maintenance process, and a cock which is manually opened/closed is secured to the drip hole 82.

The inside of the water stock tank 51 is compartmented by a partition wall 64. A penetration hole is formed in the partition wall 64, and the scale filter 66 is secured to the penetration hole. That is, the inside of the water stock tank 51 is compartmented into the chamber at the electrolytic unit 52 side and the chamber at the electrolytic water supply port 88 side by the scale filter 66, and the electrolytic water flows from the chamber at the electrolytic unit 52 side through the scale filter 66 to the other chamber. Plural float switches FS are secured at different height positions in the chamber at the downstream side of the scale filter 66.

According to this embodiment, the electrolytic water circulating and supplying portion 5 equipped to the air conditioner 110 comprises the water stock tank 51, the electrolytic unit 52 which is secured to the water stock tank 51 and electrolyzes water in the water stock tank 51 to generate electrolytic water, the water feeding pump 53 for supplying the electrolytic water generated in the electrolytic unit 52 to the outside, and the electrical component box 30 in which the power supply circuit portion 33 for supplying power to the electrolytic unit 52 and the water feeding pump 53 is mounted. The electrical component box 30 is fixed so as to be floated from the bottom surface of the case 50, and the water feed pump 53 is disposed at the lower side of the electrical component box 30. Accordingly, the electrical component box 30 in which the power supply circuit portion 33 is mounted is fixed to be floated from the bottom surface of the case 50 while the water stock tank 51, the electrolytic unit 52, the water feeding pump 53 and the electrical component box 30 containing the power supply circuit portion 33 are accommodated in the case 50. Therefore, invasion of water and electrolytic water into the power supply circuit portion 33 can be prevented, and thus the power supply circuit portion 33 can be surely protected. Accordingly, the respective portions constituting the electrolytic water circulating and supplying portion 5 can be accommodated in one case 50. Therefore, excellent maintenance performance can be secured, the lengths of the wires between the power supply circuit portion 33 and each of the electrolytic unit 52 and the water feeding pump 53 can be shortened, and the wires can be efficiently laid out.

Furthermore, the electrolytic water circulating and supplying portion 5 has the brine tank 59 for stocking brine and a supply pump 61 for supplying brine from the brine tank 59 to the water stock tank 51. As described above, this embodiment has the following specific arrangement for the respective elements constituting the electrolytic water circulating and supplying portion 5. The brine tank 59 and the water stock tank 51 are arranged in juxtaposition with each other at one side of the case 50, the water feeding pump 53 and the supply pump 61 are arranged in juxtaposition with each other below the electrical component box 30, and the water feeding pump 53 is located at the water stock tank 51 side.

Therefore, the invasion of water, electrolytic water or brine into the power supply circuit portion 33 can be prevented while the brine tank 59 and the supply pump 61 are arranged in the same case 50 as the electrical component box 30, and thus excellent maintenance performance can be secured. Furthermore, the brine tank 59 and the water stock tank 51 are arranged at one side of the case 50, and the water feeding pump 53 is located at the water stock tank 51 side below the electrical component, so that the pipe between the water feeding pump 53 and the water stock tank 51 may be designed at a short length, the layout of the pipes can be efficiently performed, and also the power loss of the pump can be suppressed.

Furthermore, in the electrolytic water circulating and supplying portion 5, the electrical component box side panel 50C which can be opened (released) is provided at one side surface of the side surfaces of the case 50 which is far away from the water stock tank 51 and the brine tank 59, and the cover of the electrical component box 30 is exposed under the open (release) state of the electrical component box side panel 50C, so that the inside of the electrical component box 30 can be accessed by opening the cover. Therefore, the access to the power supply circuit portion 33 is facilitated, and the excellent maintenance performance can be secured. Furthermore, the electrical component box side panel 50C is located at the side far from the water stock tank 51 and the brine tank 59, and the invasion of water, electrolytic water or brine can be prevented at the access time to the power supply circuit portion 33, so that the power supply circuit portion 33 can be surely protected.

Furthermore, the case 50 has the lid 50A covering the upper ends of the upper surface and the respective side surfaces of the case 50, and the electrical component box side panel 50C is allowed to be opened under the state that the lid 50A is opened. Therefore, in such a case that the electrolytic water circulating and supplying portion 5 is installed outdoors, the invasion of water or the like into the power supply circuit portion 33 can be prevented, and the excellent maintenance performance can be secured while the power supply circuit portion 33 can be surely protected when it is set outdoors or the like.

According to this embodiment, in the air filtering unit 150 having the electrolytic water circulating and supplying portion 5, the respective portions constituting the respective elements constituting the electrolytic water circulating and supplying portion 5 can be accommodated in one case 50. Therefore, the excellent maintenance performance can be secured, and further the wire between the power supply circuit portion 33 and each of the electrolytic unit 52 and the water feeding pump 53 may be designed to be short in length, so that the layout of wires can be efficiently performed.

Furthermore, according to this embodiment, the air filtering chamber 120 intercommunicating with the plural air blow-out ports 104 opened to the theater 100 as a large space through the air supply duct 105 is provided on the rooftop of the building 200 having the large space. In addition, the air filtering portion 4 is provided in the air filtering chamber 120 and the electrolytic water circulating and supplying portion 5 for supplying electrolytic water to the air filtering portion 4 in the air filtering chamber 120 is set on the rooftop together with the air filtering chamber 120. Accordingly, the air in the large space can be cleaned.

Here, with respect to the electrolytic water circulating and supplying portion 5 set on the rooftop, the excellent maintenance performance can be secured, and the efficient lay-out of wires can be implemented. Furthermore, the invasion of water or electrolytic water into the power supply circuit portion 33 can be prevented, and the power supply circuit portion 33 can be surely protected. Therefore, the air filtering unit 150 for cleaning the air in the large space can be easily implemented at a low cost.

The present invention is not limited to the above-described embodiment. In the above embodiment, the gas-liquid contact members 41A1, A2 to 41F1, F2 are arranged in the air filtering chamber 120 formed in the roof top type air conditioner 110, however, this invention is not limited to this style. For example, it is needless to say that a chamber is provided in the air supply duct 105 through which the air conditioner 110 and the air blow-out ports 104 formed in the ceiling portion 103 of the theater 100, and the gas-liquid contact members are arranged in this chamber.

Furthermore, the above embodiment adopts the water circulation system for returning the water received at the drain pan 44 through the circulating passage (the circulating water return passage) 55 to the water stock tank 51. However, the water received at the drain pan 44 may be directly discharged to the outside. In this construction, the water consumption amount is larger than that in the water circulation system, however, it is unnecessary to provide the circulating passage 55, so that the equipment cost can be reduced more greatly.

Still furthermore, the gas-liquid contact members 41A1, A2 to 41F1, F2 are arranged to be lined up in the vertical direction, and the gas-liquid contact members (for example, 41F1, F2) covering the lower area A of the air flow passage 120A are successively displaced to the upstream side of the air flow passage 120A with respect to the gas-liquid contact members (for example, 41A1, A2) covering the upper area B of the air flow passage 120A. However, this invention is not limited to this style, and it is needless to say that the gas-liquid contact members (for example, 41F1, F2) covering the lower area A of the air flow passage 120 are successively displaced to the downstream side of the air flow passage 120A with respect to the gas-liquid contact members (for example 41A1, a2) covering the upper area B of the air flow passage 120A.

Still furthermore, as described with reference to FIGS. 8 and 9, in the above embodiment, the electrical component box 30 is fixed to the side surface of the case 50 of the electrolytic water circulating and supplying portion 5. However, this invention is not limited to this style. The electrical component box 30 may be fixed so as to be floated from the bottom surface 50D by supporting the electrical component box 30 with a pole or leg. Furthermore, the shape of the case 50 is not limited to a rectangular parallelepiped, and it may be polygonal or a partially cut-out rectangular parallelepiped. The same is also applied to the shapes of the water stock tank 51, the brine tank 59, the electrical component box 30, etc. The other pipe constructions and the constructions of the other minute portions may be arbitrarily changed.

What is claimed is:

1. An air filtering apparatus for filtering air, comprising:
  a chamber having an air flow passage through which air flows, the chamber being connected through an air supply duct to a plurality of air blow-out ports opened to a large space;
  an air filtering portion that is disposed in the chamber and has a plurality of gas-liquid contact members for bringing air into contact with electrolytic water to filter the air;
  a water tank that is connected through a water feeding pump to a supply pipe for supplying the electrolytic water to each of the gas-liquid contact members of the air filtering portion;
  an electrolytic unit for generating the electrolytic water;
  a mechanism for leading to the electrolytic unit a part of electrolytic water in the water tank which is sucked by the water feeding pump and supplied to the plurality of gas-liquid contact members through the supply pipe, electrolyzing the part of the electrolytic water in the electrolytic unit to further generate electrolytic water and returning the generated electrolytic water into the water tank; and
  a drain hose that extends from a bottom of each of the plurality of gas-liquid contact members and that leads the electrolytic water from each of the plurality of gas-liquid contact members to a drain pan,
  wherein the plurality of gas-liquid contact members are arranged to be sequentially displaced in a vertical direction, and gas-liquid contact members of the plurality of gas-liquid contact members covering a lower area of the air flow passage are arranged to be displaced to one of the upstream and downstream sides of air flow through the air flow passage with respect to gas-liquid contact members of the plurality of gas-liquid contact members covering an upper area of the air flow passage.

2. The air filtering apparatus according to claim 1, wherein the plural gas-liquid contact members are arranged so as to cover substantially the whole cross-sectional area of the air flow passage in the chamber.

3. The air filtering apparatus according to claim 2, wherein a lower end of each of the plurality of gas-liquid contact members is connected through an air leading plate to an upper end of an adjacent gas-liquid contact member of the plurality of gas-liquid contact members at the upstream side of the air flow through the air flow passage so that a gap between the adjacent gas-liquid contact members is closed.

4. The air filtering apparatus according to claim 2, wherein the plurality of gas-liquid contact members are sequentially displaced in the vertical direction with a portion of each of the plurality of gas-liquid contact members overlapping each other in an air flow direction, an air leading plate is obliquely-disposed between adjacent ones of the plurality of gas-liquid contact members and closing a gap between a lower end portion of the gas-liquid contact member located at an upper position and an upper end portion of the gas-liquid contact member located at a lower position, and the plurality of gas-liquid contact members and the air leading plates are arranged as a zigzag pattern in side view.

5. An air conditioning and filtering apparatus for air-conditioning and filtering air, comprising:
  an air conditioner connected through an air supply duct to a plurality of air blow-out ports opened to a large space and supplying air-conditioned air through the air supply duct to each of the air blow-out ports;
  an air flow passage through which the air conditioner and each of the plural air blow-out ports are connected to each other and the air-conditioned air flows;
  a chamber provided in the air flow passage;
  an air filtering portion that is provided in the chamber and has a plurality of gas-liquid contact members for bringing the air-conditioned air into contact with electrolytic water to filter the air-conditioned air;
  a water tank that is connected through a water feeding pump to a supply pipe for supplying the electrolytic water to each of the gas-liquid contact members of the air filtering portion;
  an electrolytic unit for generating the electrolytic water; and
  a mechanism for leading to the electrolytic unit a part of electrolytic water in the water tank which is sucked by the water feeding pump and supplied to the plurality of gas-liquid contact members through the supply pipe, electrolyzing the part of the electrolytic water in the electrolytic unit to further generate electrolytic water and returning the generated electrolytic water into the water tank; and
  a drain hose that extends from a bottom of each of the plurality of gas-liquid contact members and that leads the electrolytic water from each of the plurality of gas-liquid contact members to a drain pan,
  wherein the plurality of gas-liquid contact members are arranged to be sequentially displaced in a vertical direction, and gas-liquid contact members of the plurality of gas-liquid contact members covering a lower area of the air flow passage are arranged to be displaced to one of the upstream and downstream sides of air flow through the air flow passage with respect to gas-liquid contact members of the plurality of gas-liquid contact members covering an upper area of the air flow passage.

6. The air conditioning and filtering apparatus according to claim 5, wherein the electrolytic unit for generating the electrolytic water is directly secured to the water tank so that scale type materials generated in the electrolytic unit are returned into the water tank together with the electrolytic water.

7. The air conditioning and filtering apparatus according to claim 5, wherein the air conditioner has a housing, and the housing is compartmented into an heat exchanger chamber in which a heat exchanger and an air blower are mounted, a machine chamber in which a compressor is mounted and an air filtering chamber containing the chamber, the air conditioned air being circulated through the chamber.

8. The air conditioning and filtering apparatus according to claim 5, wherein the air supply duct is connected to the chamber, and the plural gas-liquid contact members are arranged so as to cover substantially the whole cross-sectional area of the air flow passage in the chamber.

9. The air conditioning and filtering apparatus according to claim 8, wherein the lower end of each gas-liquid contact member is connected through an air leading plate to the upper end of the gas-liquid contact member which is adjacent to the former gas-liquid contact member at the upstream side of air flow through the air flow passage so that the gap between both the gas-liquid contact members is closed.

10. The air conditioning and filtering apparatus according to claim 9, wherein the plurality of gas-liquid contact members are sequentially displaced in the vertical direction with a portion of each of the plurality of gas-liquid contact members overlapping each other in an air flow direction, an air leading plate is obliquely-disposed between adjacent ones of the plurality of gas-liquid contact members and closing a gap between a lower end portion of the gas-liquid contact member located at an upper position and an upper end portion of the gas-liquid contact member located at a lower position, and the plurality of gas-liquid contact members and the air leading plates are arranged as a zigzag pattern in side view.

* * * * *